US010287271B2

United States Patent
Kunick et al.

(10) Patent No.: US 10,287,271 B2
(45) Date of Patent: May 14, 2019

(54) INDOLE COMPOUNDS HAVING ANTIPROTOZOAL ACTIVITY AND ITS USE AS WELL AS METHODS FOR PRODUCING THE SAME

(71) Applicants: TECHNISCHE UNIVERSITAET BRAUNSCHWEIG, Braunschweig (DE); YISSUM RESEARCH DEVELOPMENT COMPANY OF THE HEBREW UNIVERSITY OF JERUSALEM LTD., Jerusalem (IL)

(72) Inventors: Conrad Kunick, Hamburg (DE); Hoang Lande, Braunschweig (DE); Johann Gruenefeld, Ribbesbuettel (DE); Ron Dzikowski, Jerusalem (IL); Abed Nasereddin, Jerusalem (IL)

(73) Assignees: TECHNISCHE UNIVERSITAET BRAUNSCHWEIG, Braunschweig (DE); YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 0 days.

(21) Appl. No.: 15/741,862

(22) PCT Filed: Jul. 10, 2015

(86) PCT No.: PCT/EP2015/065812
§ 371 (c)(1),
(2) Date: Jan. 4, 2018

(87) PCT Pub. No.: WO2017/008826
PCT Pub. Date: Jan. 19, 2017

(65) Prior Publication Data
US 2018/0194750 A1 Jul. 12, 2018

(51) Int. Cl.
| C07D 403/08 | (2006.01) |
| C07D 209/12 | (2006.01) |
| A61P 33/06 | (2006.01) |
| C07D 401/08 | (2006.01) |
| C07D 471/04 | (2006.01) |

(52) U.S. Cl.
CPC ............ C07D 403/08 (2013.01); A61P 33/06 (2018.01); C07D 209/12 (2013.01); C07D 401/08 (2013.01); C07D 471/04 (2013.01)

(58) Field of Classification Search
CPC .................................................. C07D 403/08
See application file for complete search history.

(56) References Cited

PUBLICATIONS

Jane E. Sykes and Mark G. Papich Chapter 10—"Antiprotozoal Drugs" in Canine and Feline Infectious Diseases 2014, p. 97.*

Biamonte et al: "Recent advances in malaria drug discovery", Bioorganic & Medicinal Chemistry Letters, vol. 23, pp. 2829-2843, Mar. 27, 2013.
Faul et al: "A General Approach to the Synthesis of Bisindolylmaleimides: Synthesis of Staurosporing Aglycone", Synthesis, pp. 1511-1516, Dec. 1995.
Green et al: "Synthesis of 1,2-Diphenylcyclobutene-3,4dione", Sythensis, pp. 46-47, Jan. 1974.
Liu et al: "Synthesis and antitumor activity of novel 3,4-diaryl squaric acid analogs", European Journal of Medicinal Chemistry, vol. 65, pp. 187-194, May 2, 2013.
Lunelli: "New, optimized preparation of 1,2-dichlorocyclobuten-3,4-dione (C4O2Cl2) from squaric acid and oxalyl chloride", Tetrahedron Letters, vol. 48, pp. 3595-3597, Mar. 21, 2007.
Matsuoka et al: "Syntheses of 3,4-Bisaryl-3-cyclobutene-1,2-diones and Related Heterocycles", Dyes and Pigments, vol. 16, pp. 309-315, Feb. 1, 1991.
Murray et al: "Global malaria mortality between 1980 and 2010: a systematic analysis", Lancet, vol. 379, pp. 413-431, Feb. 4, 2012.
Ried et al: "Reaktionen mit Cyclobutendionen, XXXIV. Mitteilung. Acylierung von Indolizinen", Synthesis, pp. 670-671, Sep. 1974.
Schlitzer: "Antimalarial Drugs—What is in Use and What is in the Pipeline", Arch. Pharm. Chem. Life Sci., vol. 341, pp. 149-163, 2008.
Schlitzer: "Malaria Chemotherapeutics Part 1: History of Antimalarial Drug Development, Currently Used Therapeutics, and Drugs in Clinical Development", Chemmedchem, vol. 2, pp. 944-986, 2007.
Schmidt et al: "Oxocarbons and related compounds. Part 24. Chlorosquarylation of indoles", J. Chem. Soc., Perkin Trans.1, pp. 495-496, Jan. 11, 1996.

(Continued)

*Primary Examiner* — David K O'Dell
(74) *Attorney, Agent, or Firm* — W&C IP

(57) ABSTRACT

In a first aspect, the present invention relates to new compounds as depicted in formula (I). In particular, compounds according to the present invention are bisindolylcyclobutendione-based structures having antiprotozoal activity. In a further aspect, pharmaceutical compositions containing the same are provided as well as the use of the compounds and pharmaceutical compositions for the prophylaxis and treatment of parasite based diseases including malaria. Finally, methods for the treatment of parasite diseases including malaria are provided.

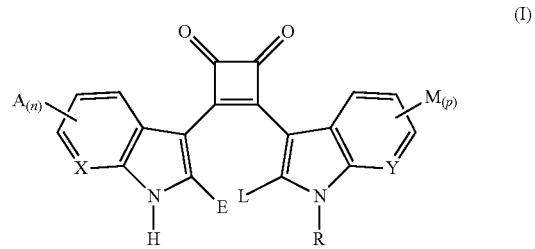

33 Claims, No Drawings

(56) References Cited

PUBLICATIONS

Shirinyan et al: "Photochromic Dihetarylethenes. 8*. A novel route to the synthesis of 3,4-bis(2,5-dimethyl-3-thienyl)furan-2,5-dione as a potential photochrome*2, Chemisty of Heterocyclic Compounds", vol. 37, No. 1, pp. 77-84, 2001.
Treibs et al: "Cyclobutenderivate der Pyrrolreihe", Liebigs Ann. Chem., pp. 153-167, 1966.
Zhang et al: "An Effective Procedure for the Acylation of Azaindoles at C-3", J. Org. Chem., vol. 67, pp. 6226-6227, Jul. 20, 2002.

* cited by examiner

INDOLE COMPOUNDS HAVING ANTIPROTOZOAL ACTIVITY AND ITS USE AS WELL AS METHODS FOR PRODUCING THE SAME

In a first aspect, the present invention relates to new compounds as depicted in formula (I). In particular, compounds according to the present invention are bisindolylcyclobutenedione-based structures having antiprotozoal activity. In a further aspect, pharmaceutical compositions containing the same are provided as well as the use of the compounds and pharmaceutical compositions for the prophylaxis and treatment of parasite based diseases including malaria. Finally, methods for the treatment of parasite diseases including malaria are provided.

PRIOR ART

Although in recent years progress has been made in the therapy of infectious diseases in the western industrial world, people namely in the developing countries suffer from parasitic infectious diseases. Among these tropical infections, malaria is one of the most important and widespread, causing in 2013 198 million clinical cases with 584.000 fatalities [WHO, World Malaria Report 2014]. Young children and pregnant women in tropical African countries are especially affected by the deadly disease. Malaria is caused by protozoal parasites of the genus *Plasmodium* (*P. falciparum, P. knowlesi, P. ovale, P. malaria, P. vivax*) which are transmitted during the bite of female *Anopheles* mosquitoes. Among the different varieties of the disease, Malaria tropica, caused by *P. falciparum*, is the most dangerous [M. Schlitzer, ChemMedChem 2 (2007) 944-986; C. J. Murray et al., Lancet 379 (2012) 413-431]. The drugs used for propylaxis and treatments of malaria currently comprise 4-aminoquinolines (chloroquine, amodiaquine, piperaquine), 8-aminoquinolines (primaquine, ebulaquine), arylamino alcohols (quinine, halofantrine, mefloquine, lumefantrine), naphthoquinones (atovaquone), sulfones and sulfonamides (dapsone, sulfadoxine), open-chain and cyclized biguanides (proguanil and chlorocycloguanil), antifolates (pyrimethamine) and antibiotics (doxycycline, clindamycin). The artemisinines are a family of cyclic peroxides (artemether, artesunate) constituting the most important compound family currently used as antimalarial drugs [M. Schlitzer, Arch. Pharm. Chem. Life Sci. 341 (2008) 149-163; M. A. Biamonte, J. Wanner, K. G. Le Roch, Bioorg. & Med. Chem. Lett. 23 (2013) 2829-2843]. Artemisinine-based combination therapy (ACT) is established as standard medication for malaria treatment in many countries (e.g. artemether/lumefantrine or artesunate/amodiaquine combinations). The importance of this therapy regime is reflected by the number of ACT treatment courses, which increased from 11 million in 2005 to 392 million in [WHO, World Malaria Report 2014]. The most important problems encountered with medicinal antimalarial treatment are severe unwanted side effects on the one hand and development of resistance on the other hand. Resistance development is inevitable to almost every therapy with antiinfective drugs [M. Schlitzer, ChemMedChem 2 (2007) 944-986]. The development of resistance against artemisinine drugs in South East Asia is alarming and has already led to the replacement of ACT for an atovaquone/proguanil regime in some regions [WHO, World Malaria Report 2014]. A further increase of artemisinine resistance could lead to a disastrous proliferation of malaria in the world. To face the problems with resistance and to avoid cross-resistance in the future, there is an urgent need for new antimalarial drugs with novel modes of action. In this regard, a number of compound classes representing different chemotypes and antiplasmodial molecular mechanisms are currently in development, e.g. 4-aminoquinolines (e.g. ferroquine and tafenoquine), endoperoxides (e.g. derivatives of OZ277), phosphatidylcholine inhibitors (e.g. SAR97275), dihydrofolate reductase inhibitors (e.g. P218), electron transport chain blockers (e.g. ELQ-300), spiroindolones (e.g. NITD609/KAE609), purine nucleoside phosphorylase inhibitors (e.g. BX4945), triazolopyrimidines (e.g. DSM265), imidazolopiperazines (e.g. GNF156/KAF156), and 3,5-diaryl-2-aminopyridines (e.g. MMV390048) [D. S. Barnett, R. K. Guy, Chem. Rev. 114 (2014) 11221-11241]. In spite of these efforts, the number of new antimalarial drugs that eventually reach the market and constitute an option to fight resistant *Plasmodium* parasites is low. It is therefore beyond doubt necessary to intensify efforts to find novel antimalarial drugs with new chemical structures.

Malaria in human is based on the following group of Plasmodia, namely, *Plasmodium falciparum, Plasmodium knowlesi, Plasmodium malariae, Plasmodium vivax* and *Plasmodium ovale*, whereby *Plasmodium falciparum* is the most occurring and most virulent *plasmodium* thereof.

Another example of infectious disease caused by protozoa is toxoplasmosis. The causing agent is *Toxoplasma gondii*, a protozoon of the subclass of coccidiae. It is assumed that about 25 to 30% of the world population is chronically infected with *toxoplasma*. In immune suppressed or immune compromised individuals toxoplasmosis may occur as an opportunistic disease, e.g. in HIV patients where cellular toxoplasmosis is a life threatening disease. Also in recipients of transplants where a therapeutically induced immune suppression is present, toxoplasmosis is life threatening.

In addition, toxoplasmosis is of importance in the veterinary field. For example, during pregnancy of sheep, high rate of miscarriages may occur. Other coccidiae representing relevant pathogens or causative agents in human and animals are from the genera of *Eimeria, Isospora, Sarcocystis, Hamondia, Neospora* and *Cryptosporidium*. Further veterinary disease causing agents include *Eimeria* (poultries), *Neospora* (canine), Cryptosporidia (calves). In particular, coccidosis may cause high losses in poultry.

All of the protozoae mentioned above, namely Plasmodia and Coccidia are members of *Apicomplexa*, a group of parasites having the same ancient offspring and being characterized of residing most of their lifetime intracellular. Another important group of parasitic protozoa are flagellates responsible for infectious diseases. For example, infections with *Trypanosoma cruzi*, the causing agent of chagas disease, infections with *Trypanosoma brucei*, the causing agent of the sleeping sickness and infection with *Leishmania*.

The problem to be solved was the provision of a new chemotype with antiprotozoal activity, like antiplasmodial activity.

The solution of the problem was the invention of 3,4-bis(indol-3-yl)cyclobut-3-ene-1,2-diones, which are at least unsubstituted at one of two nitrogens. To our best knowledge, this compound class was not described or mentioned in the literature before.

The 3,4-bis(indol-3-yl)cyclobut-3-ene-1,2-diones, which are at least unsubstituted at one of two nitrogens resulted from a screening campaign directed to find a novel antiplasmodial chemotype. Neither the chemical compound class nor its antiplasmodial activity have been reported before. As shown in table 1, several derivatives of the general formula I inhibit the growth of *Plasmodium falciparum* parasites in single digit micromolar to submicromolar concentrations.

In this specification a number of documents including patent applications and manufacture's manuals are cited. The disclosures of these documents, while not considered relevant for the patentability of this invention is herewith incorporated by reference in its entirety. More specifically, all the referenced documents are incorporated by reference to the same extent as if each individual document was specifically and individually indicated to be incorporated by reference.

BRIEF DESCRIPTION OF THE PRESENT INVENTION

In a first aspect, the present invention provides a compound of formula (I)

(I)

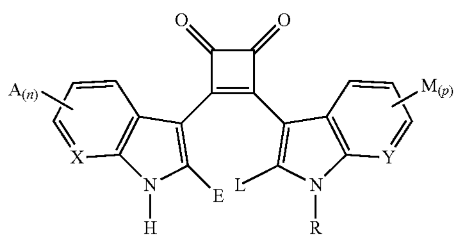

wherein X, Y are independently of each other, C, N or C—R;
L is hydrogen, $C_1$-$C_8$ alkyl, $C_1$-$C_8$ alkyloxy, aryloxy, halogen, formyl, aryl including phenyl, heteroaryl including pyridyl, heterocycloalkyl, acyl, hydroxy $C_1$-$C_8$ alkyl, halo $C_1$-$C_8$ alkyl, amino $C_1$-$C_8$ alkyl;
E is hydrogen, $C_1$-$C_8$ alkyl, $C_1$-$C_8$ alkyloxy, aryloxy, halogen, formyl, aryl including phenyl, heteroaryl including pyridyl, heterocycloalkyl, acyl, hydroxy $C_1$-$C_8$ alkyl, halo $C_1$-$C_8$ alkyl, amino $C_1$-$C_8$ alkyl;
A is independently of each other, halogen, hydroxyl, amino, monoalkylamino, dialkylamino, sulfanyl, sulfinyl, sulfonyl, aminosulfonyl, carboxyl, $C_1$-$C_8$ alkyloxy, aryloxy, nitro, cyano, $C_1$-$C_8$ alkyl, amino $C_1$-$C_8$ alkyl, hydroxy $C_1$-$C_8$ alkyl, halo $C_1$-$C_8$ alkyl including trifluoromethyl, halo $C_1$-$C_8$ alkyloxy including trifluoromethoxy, carbonylamino, aminocarbonyl, acyl, formyl, aryl including phenyl, heteroaryl including pyridyl, heterocycloalkyl; M is independently of each other, halogen, hydroxyl, amino, monoalkylamino, dialkylamino, sulfanyl, sulfinyl, sulfonyl, aminosufonyl, carboxyl, $C_1$-$C_8$ alkyloxy, aryloxy, nitro, cyano, $C_1$-$C_8$ alkyl, amino $C_1$-$C_8$ alkyl, hydroxy $C_1$-$C_8$ alkyl, halo $C_1$-$C_8$ alkyl including trifluoromethyl, halo $C_1$-$C_8$ alkyloxy including trifluoromethoxy, carbonylamino, aminocarbonyl, acyl, formyl, aryl including phenyl, heteroaryl including pyridyl, heterocycloalkyl;
R is hydrogen, Z or Q;
Z is $C_1$-$C_8$ alkyl, hydroxy $C_1$-$C_8$ alkyl, methoxy $C_1$-$C_8$ alkyl, halo $C_1$-$C_8$ alkyl, amino $C_1$-$C_8$ alkyl, acyl, sulfinyl $C_1$-$C_8$ alkyl, sulfonyl $C_1$-$C_8$ alkyl;
Q is aryl preferably phenyl, or heteroaryl or heterocycloalkyl, which may be substituted by a substituent as listed for Z;
n is 0 or is an integer of 1, 2, or 3,
p is 0 or is an integer of 1, 2, or 3,
or a salt or solvate thereof.

For example, the compounds of the formula (I) are compounds wherein X and Y are C, R is H or $CH_3$, A is independently from each other hydrogen, $CH_3$, phenyl, cyano, Br or I, M is independently from each other hydrogen, $CH_3$, phenyl, cyano, Br or I, L and E are independently from each other $CH_3$, hydrogen or phenyl and n and p are independently from one another 0 or 1.

In a further aspect, the present invention provides a pharmaceutical composition comprising one or more compounds according to the present invention. The present inventors recognized that the compounds according to the present invention display favourable activity on protozoae, in particular, on protozoae of the genus of *Apicomplexa*. As demonstrated, the compounds have a strong effect on *Plasmodium*, thus, allowing treatment of malaria accordingly. The compounds according to the present invention inhibit the growth of *Plasmodium falciparum* parasites in single digit micromolar to submicromolar concentrations.

Hence, in another aspect, the present invention relates to the use of the compounds according to the present invention for treating or preventing a disease caused by a parasite of *Apicomplexa*. The compounds are particularly useful for treating or preventing an infection by a parasite and a disease of:

a) *Plasmodium* and malaria said parasite being preferably *Plasmodium falciparum;*
b) *Toxoplasma gondii* and toxoplasmosis;
c) *Eimeria* and coccidiosis;
d) *Isospora* and isosporiasis/coccidiosis
e) *Babesia* and babesiosis;
f) *Cyclospora* and cyclosporiasis;
g) *Cryptosporidium* and cryptosporidiosis;
h) *Theileria* and theileriaosis;
i) *Neospora* and neosporosis;
j) *Sarcocystis/Hoareosporidium* and sarcocystiosis.

In another aspect, the present invention relates to a pharmaceutical composition comprising at least one compound according to the present invention in combination with antiprotozoal active compounds known in the art. This pharmaceutical composition may be adapted in form of allowing simultaneous, separate or sequential administration of the compounds accordingly. In an embodiment thereof, the pharmaceutical compositions are compositions being formulated in a way that the compounds of the present invention are present in a sub antiprotozoal dosage as it is the case for the at least one further antiprotozoal active agent accordingly.

DETAILED DESCRIPTION OF THE PRESENT INVENTION

In a first aspect, the present invention relates to a compound of formula (I)

(I)

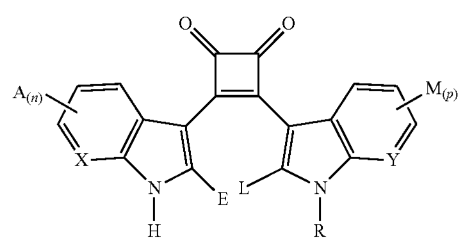

wherein X, Y are independently of each other, C, N or C—R;
L is hydrogen, $C_1$-$C_8$ alkyl, $C_1$-$C_8$ alkyloxy, aryloxy, halogen, formyl, aryl including phenyl, heteroaryl including pyridyl, heterocycloalkyl, acyl, hydroxy $C_1$-$C_8$ alkyl, halo $C_1$-$C_8$ alkyl, amino $C_1$-$C_8$ alkyl;

E is hydrogen, $C_1$-$C_8$ alkyl, $C_1$-$C_8$ alkyloxy, aryloxy, halogen, formyl, aryl including phenyl, heteroaryl including pyridyl, heterocycloalkyl, acyl, hydroxy $C_1$-$C_8$ alkyl, halo $C_1$-$C_8$ alkyl, amino $C_1$-$C_8$ alkyl;

A is independently of each other, halogen, hydroxyl, amino, monoalkylamino, dialkylamino, sulfanyl, sulfinyl, sulfonyl, aminosulfonyl, carboxyl, $C_1$-$C_8$ alkyloxy, aryloxy, nitro, cyano, $C_1$-$C_8$ alkyl, amino $C_1$-$C_8$ alkyl, hydroxy $C_1$-$C_8$ alkyl, halo $C_1$-$C_8$ alkyl including trifluoromethyl, $C_1$-$C_8$ alkyloxy including trifluoromethoxy, carbonylamino, aminocarbonyl, acyl, formyl, aryl including phenyl, heteroaryl including pyridyl, heterocycloalkyl; M is independently of each other, halogen, hydroxyl, amino, monoalkylamino, dialkylamino, sulfanyl, sulfinyl, sulfonyl, aminosufonyl, carboxyl, $C_1$-$C_8$ alkyloxy, aryloxy, nitro, cyano, $C_1$-$C_8$ alkyl, amino $C_1$-$C_8$ alkyl, hydroxy $C_1$-$C_8$ alkyl, halo $C_1$-$C_8$ alkyl including trifluoromethyl, halo $C_1$-$C_8$ alkyloxy including trifluoromethoxy, carbonylamino, aminocarbonyl, acyl, formyl, aryl including phenyl, heteroaryl including pyridyl, heterocycloalkyl;

R is hydrogen, Z or Q;

Z is $C_1$-$C_8$ alkyl, hydroxy $C_1$-$C_8$ alkyl, methoxy $C_1$-$C_8$ alkyl, halo $C_1$-$C_8$ alkyl, amino $C_1$-$C_8$ alkyl, acyl, sulfinyl $C_1$-$C_8$ alkyl, sulfonyl $C_1$-$C_8$ alkyl;

Q is aryl preferably phenyl, or heteroaryl or heterocycloalkyl, which may be substituted by a substituent as listed for Z;

n is 0 or is an integer of 1, 2, or 3, p is 0 or is an integer of 1, 2, or 3, or a salt or solvate thereof.

That is, the present inventors have recognized that administering of the compounds according to the present invention allows to treat or prevent a disease caused by a parasite of the group of *apicomplexa* or flagellates. In particular, the present inventors recognized that the compounds of the present invention have antiprotozoal activity, like antiplasmodial activity.

In the context of the present invention, the term "comprising", "comprises", "containing" or "contains" include the embodiments of "consisting of" or "consist".

The term "halogen" as used herein includes the halogens F, Cl, Br and I, it is preferred that the halogen is Cl or Br or I.

The term "$C_1$ to $C_8$" as used herein include compounds having $C_1$, $C_2$, $C_3$, $C_4$, $C_5$, $C_6$, $C_7$ or $C_8$ carbon atoms. The term "$C_1$ to $C_6$" include $C_1$, $C_2$, $C_3$, $C_4$, $C_5$, $C_6$ carbon atoms. The term "$C_1$ to $C_3$" include, $C_1$, $C_2$ or $C_3$ carbon atoms. The groups may be present in linear, branched or cyclic form.

The term "Alkyl" refers to a saturated aliphatic hydrocarbon including straight chain and branched chain groups. The alkyl group may be a $C_1$-$C_8$ alkyl group, like a $C_1$-$C_3$ alkyl group. "Alkyl" may be exemplified by groups such as methyl, ethyl, n-propyl, isopropyl, n-butyl and the like. Alkyl groups may be substituted or unsubstituted. Substituents may also be themselves substituted. When substituted, the substituent group is preferably, but not limited to, $C_1$-$C_3$ alkyl, aryl, amino, cyano, halogen, $C_1$-$C_3$ alkoxy or hydroxyl.

"Acyl" or "carbonyl" refers to the group —C(O)R wherein R is H, $C_1$-$C_8$ alkyl, like $C_1$-$C_3$ alkyl, aryl, heteroaryl, carbocyclic, heterocarbocyclic, $C_1$-$C_8$ alkyl aryl or $C_1$-$C_8$ alkyl heteroaryl.

"Alkoxy" refers to the group —O—R wherein R is acyl, alkyl, like $C_1$-$C_8$ alkyl, e.g. $C_1$-$C_3$ alkyl, aryl, carbocyclic, heterocarbocyclic, heteroaryl, $C_1$-$C_8$ alkyl aryl or $C_1$-$C_8$ alkyl heteroaryl.

"Aralkyl" refers to a radical in which an aryl group is substituted for a hydrogen atom of an alkyl group; e.g., $C_6H_5CH_2$—.

"Amino" refers to the group —NR'R" wherein R' and R" are each, independently, hydrogen, alkyl, aryl, heteroaryl, $C_1$-$C_3$ alkyl aryl or $C_1$-$C_3$ alkyl heteroaryl. The R' and R" groups may themselves be linked to form a ring.

"Aryl" refers to an aromatic carbocyclic group. "Aryl" may be exemplified by phenyl or benzyl or naphthyl. The aryl group may be substituted or unsubstituted. Substituents may also be themselves substituted. When substituted, the substituent group is preferably, but not limited to, alkyl, alkoxy, heteroaryl, acyl, carboxyl, amido, carbamoyl, carbonylamino, nitro, amino, cyano, halogen or hydroxyl. The substituents may be positioned at various locations on an aryl group. For example, substituents on a phenyl group may be located at an ortho-position, a meta-position, the para-position, or combinations thereof.

"Carboxyl" refers to the group —C(=O)OR, where R is a $C_1$-$C_3$ alkyl, aryl or heteroaryl. The alkyl or aryl group may be substituted or unsubstituted. Substituents may also be themselves substituted. When substituted, the substituent group is preferably, but not limited to, alkyl, alkoxy, heteroaryl, acyl, carboxyl, carbonylamino, nitro, amido, carbamoyl, amino, cyano, halogen or hydroxyl. The substituents may be positioned at various locations on an aryl group.

"Heteroaryl" or "heteroaromatic" refers to a monocyclic or bicyclic aromatic carbocyclic radical having one or more heteroatoms in the carbocyclic ring. Heteroaryl may be substituted or unsubstituted. When substituted, the substituents may themselves be substituted. Preferred, but non-limiting substituents, are aryl, $C_1$-$C_3$ alkyl aryl, amino, halogen, hydroxyl, cyano, nitro, carboxyl, carbonylamino or $C_1$-$C_3$ alkyl. Preferred heteroaromatic groups include tetrazolyl, thiazolyl, thienyl, thiophenyl, thiazolyl, purinyl, pyrimidyl, pyridyl, and furanyl. More preferred heteroaromatic groups include benzothiofuranyl, thiophenyl, thienyl, furanyl, tetrazolyl, triazolyl, and pyridyl.

"Heteroatom" means an atom other than carbon in the ring of a heterocyclic group or a heteroaromatic group or the chain of a heterogeneous group. Preferably, heteroatoms are selected from the group consisting of nitrogen, sulfur, phosphor and oxygen atoms. Groups containing more than one heteroatom may contain different heteroatoms.

"Heterocarbocyclic group" or "heterocycloalkyl" or "heterocyclic" means a monovalent saturated or unsaturated hydrocarbon ring containing at least one heteroatom. Heterocarbocyclic groups are monocyclic, or are fused, spiro, or bridged bicyclic ring systems. Monocyclic heterocarbocyclic groups contain 3 to 10 carbon atoms, preferably 4 to 7 carbon atoms, and more preferably 4 to 5 carbon atoms in the ring. Bicyclic heterocarbocyclic groups contain 8 to 12 carbon atoms, preferably 9 to 10 carbon atoms in the ring. Heterocarbocyclic groups may be substituted or unsubstituted. Suitable substituents include, but are not limited to, lower alkyl, hydroxyl, cyano, halogen and amino. Substituents may also be themselves substituted. Preferred heterocarbocyclic groups include epoxy, tetrahydrofuranyl, azacyclopentyl, azacyclohexyl, piperidyl, and homopiperidyl. More preferred heterocarbocyclic groups include piperidyl, and homopiperidyl. The most preferred heterocarbocyclic group is piperidyl. Heterocarbocyclic groups are preferably not aromatic.

It has been found surprisingly that the compounds of formula (I) wherein at least one of the nitrogen atoms present in the indole ring is unsubstituted, demonstrate antiprotozoal activity.

In a preferred embodiment, the compound of the present invention is a compound wherein substituent R is $C_1$-$C_3$ alkyl, including methyl, ethyl and propyl, or a hydrogen atom. That is, in an embodiment of the present invention, the compound according to the present invention is an N-unsubstituted derivative of 3,4-bis(indol-3-yl)cylobut-3-ene-1,2-dione, namely R is hydrogen.

Furthermore, in another embodiment, the present invention relates to a compound of formula (I) wherein the substituent A is independently from one another a halogen, cyano, $C_1$-$C_3$ alkyl, $C_1$-$C_3$ alkoxy, phenyl and/or M is independently from one another a halogen, cyano, $C_1$-$C_3$ alkyl, $C_1$-$C_3$ alkoxy, phenyl. In an embodiment of the invention, the substituents A and M are independently of each other present at position 5 of the indole ring. For example while at one indole ring system the substituent A or M may be a halogen, the substituent at the other indole ring M or A is identical or is different, like a methyl group or methoxy group.

In another embodiment of the present invention, the compound of formula (I) is a compound wherein substituent L is hydrogen or a $C_1$-$C_3$ alkyl group, or aryl in particular, hydrogen, methyl or phenyl and/or E is hydrogen or a $C_1$-$C_3$ alkyl group, or aryl in particular, hydrogen, methyl or phenyl.

Moreover, in another embodiment of the present invention, X and/or Y are a carbon atom, C. When X and/or Y, preferably both, are a carbon atom, the carbon atom may be unsubstituted or substituted. When the carbon atom is substituted, the substituent is R, namely, X and Y are C—R. R may be a hydrogen, Z or Q, as defined therein.

Moreover, n may be an integer of 1 or is 0 and/or p may be an integer of 1 or is 0. That is e.g. p is 1 while n is 0 or p is 0 while n is 1 or p and n are 1 or p and n are 0.

Furthermore, an embodiment of the present invention is a compound of formula (I) wherein X is C, Y is C, R is H or $CH_3$, M is $CH_3$, phenyl or Br or I, L is $CH_3$, hydrogen or phenyl and n is 0 or 1. Particularly useful compounds according to the present invention are depicted in formulae (II) to (XI).

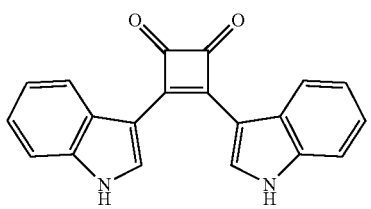

(II)

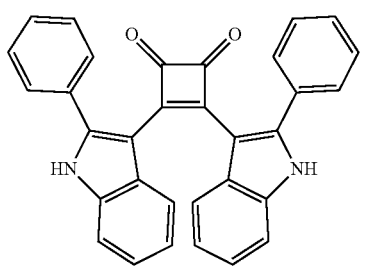

(III)

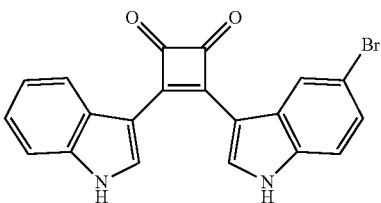

(IV)

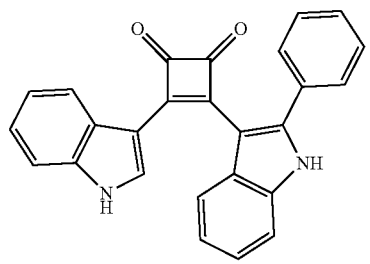

(V)

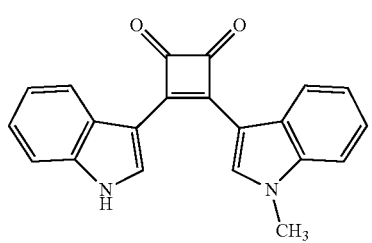

(VI)

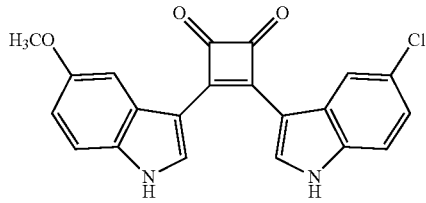

(VII)

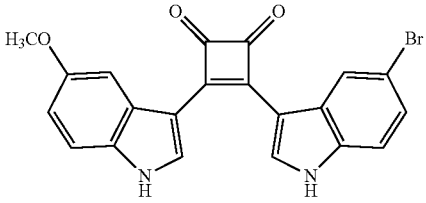

(VIII)

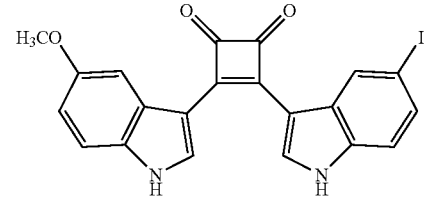

(IX)

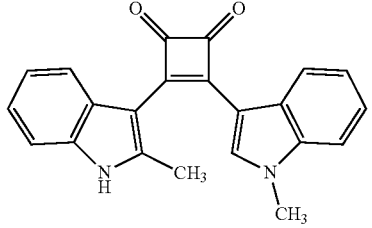

(X)

(XI)

As demonstrated in the examples, the compounds according to the present invention demonstrate antiparasitic activity, in particular, antiplasmodial activity.

The compounds of the present invention are useful for preventing and/or treating a disease caused by infection with protozoa including flagellates, like *Leishmania*, Trypanosoma, *Lamblia, Trichomonas*, or *Apicomplexa*, like *Plasmodium* or *Toxoplasma, Eimeria, Babesia, Isospora, Theileria, Neospora, Cryptosporidium*, etc. in humans and animals.

The compounds according to the present invention may be used in form of its free compounds or of salts thereof or in form of solvates, like hydrates. For example, the compounds according to the present invention may be administered in form of pharmaceutically acceptable salts thereof.

As used herein, the term "pharmaceutically acceptable salts thereof", refers to salts which are non-toxic when administered to human or animals. Salts useful according to the present invention include hydrochlorides, hydrobromides, hydroiodides, sulfates, bisulfates, nitrates, citrates, tatrates, bitatrates, phosphates, hydrogenphosphates, dihydrogenphosphates, carbonates, hydrogencarbonates, malates, maleates, fumarates, succinates, acetates, terephthalates, laurates, palmitates, pamoates, pectinates, besilates, ciclotates, closilates, esilates, gluconates, hyclates, isethionates, lactobionates, mesylates, orotates, tosylates, xinafoates as well as salts with sodium, potassium, calcium, deanol, diolamine, edamine, epolamine, erbumine, meglumine, olamine, trometamol.

The route of administration of the compounds of the present invention depends on the formulation in use. That is, the compounds according to the present invention may be administered in form of infusion, in form of capsules or other suitable forms, like tablets.

As mentioned, administration may depend on the form of the pharmaceutical composition used. For example, the pharmaceutical composition may be in solid form or fluid form for enteral or parenteral application.

As used herein, the term "sub antiprotozoal dosage" for an individual to be treated refers to a dosage which, when used alone, does not have the antiprotozoal activity in said individual. This term comprises direct application as well as a controlled release of the active ingredient. It is clear, that the sub antiprotozoal dosage of an agent is dependent on the kind of administration and the way of administration. The skilled person can determine sub antiprotozoal dosages of the active ingredient without undue burden. In particular, a sub antiprotozoal dosage is below the dose of the active ingredient, which should be used according to general recommendation of the skilled person when administered alone.

In a further embodiment, the present invention relates to a pharmaceutical composition comprising one or more compounds according to the present invention.

Preferably, the pharmaceutical composition comprising the compounds according to the present invention is intended for the treatment of humans and/or animals.

The skilled person is well aware of suitable diluents, excipients, or carriers.

The pharmaceutical composition may be administered with a physiologically acceptable carrier to a patient, as described herein. In a specific embodiment, the term "pharmaceutically acceptable" means approved by a regulatory agency or other generally recognized pharmacopoeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatine, malt, rice, flour, chalk, silica gel, sodium stearate, glycerol monostearate, talc, sodium chloride, dried skim milk, glycerol, propyleneglycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, patches and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium, carbonate, etc. Examples of suitable pharmaceutical carriers are described in "Remington's Pharmaceutical Sciences" by E. W. Martin (18th ed., Mack Publishing Co., Easton, Pa. (1990)). Such compositions will contain a therapeutically effective amount of the aforementioned compounds according to the present invention, preferably in purified form, together with a suitable amount of carrier so as to provide the form for proper administration to the patient. The formulation should suit the mode of administration.

Typically, pharmaceutically or therapeutically acceptable carrier is a carrier medium which does not interfere with the effectiveness of the biological activity of the active ingredients and which is not toxic to the host or patient.

In another preferred embodiment, the composition is formulated in accordance with routine procedures as a pharmaceutical composition adapted for intravenous or oral administration to human beings. Typically, compositions for intravenous administration are solutions in sterile isotonic aqueous buffer. Where necessary, the composition may also include a solubilizing agent and a local anaesthetic such as lidocaine to ease pain at the site of the injection. Generally, the ingredients are supplied either separately or mixed together in a unit dosage form, for example, as a dry lyophilised powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The pharmaceutical composition for use in connection with the invention can be formulated as neutral or salt forms. Pharmaceutically acceptable salts include those formed with anions such as those derived from hydrochloric, phosphoric, acetic, oxalic, tartaric acid, etc., and those formed with cations such as those derived from sodium, potassium, ammonium, calcium, ferric hydroxides, isopropylamine, triethylamine, 2-ethylamino ethanol, histidine, procaine, etc.

"Therapeutically- or pharmaceutically-effective amount" as applied to the compositions of the instant invention refers to the amount of composition sufficient to induce a desired biological result. That result can be alleviation of the signs, symptoms, or causes of a disease, or any other desired alteration of a biological system.

In vitro assays may optionally be employed to help identifying optimal dosage ranges. The precise dose to be employed in the formulation will also depend on the route of administration, and the seriousness of the disease or disorder, and should be decided according to the judgement of the practitioner and each patient's circumstances. Effective doses may be extrapolated from dose-response curves derived from in vitro or animal model test systems. Preferably, the pharmaceutical composition is administered directly or in combination with an adjuvant. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

In the context of the present invention the term "subject" means an individual in need of a therapy that can be alleviated or cured by administering the compounds according to the present invention to the individual. Preferably, the subject is a vertebrate, even more preferred a mammal, particularly preferred a human.

The term "administered" means administration of a therapeutically effective dose of the aforementioned pharmaceutical composition comprising the compounds according to the present invention.

The methods are applicable to both human therapy and veterinary applications. The compounds described herein having the desired therapeutic activity may be administered in a physiologically acceptable carrier to a patient, as described herein. Depending upon the manner of introduction, the compounds may be formulated in a variety of ways as discussed below. The concentration of therapeutically active compound in the formulation may vary from about 0.1-100 wt %. The agents may be administered alone or in combination with other treatments.

The administration of the pharmaceutical composition can be done in a variety of ways as discussed above, including, but not limited to, orally, subcutaneously, intravenously, intra-arterially, intranodally, intramedullarily, intrathecally, intraventricularly, intranasally, intrabronchially, transdermally, intrarectally, intraperitoneally, intramuscularly, intrapulmonarily, vaginally, rectally, or intraocularly. In some instances, for example, in the treatment of wounds and inflammation, the pharmaceutically effective agent may be directly applied as a solution dry spray.

The attending physician and clinical factors will determine the dosage regimen. A typical dose can be, for example, in the range of 0.001 to 2000 µg; however, doses below or above this exemplary range are envisioned, especially considering the aforementioned factors.

In an embodiment of the present invention, the compounds according to the present invention are the only pharmaceutical active agent comprised in said pharmaceutical composition. Moreover, in another embodiment of the present invention, the pharmaceutical composition according to the present invention may contain at least one further antiprotozoal active agent. The at least one further antiprotozoal active agent may be an antiprotozoal agent known in the art. For example, the at least one further antiprotozoal active agent is selected from the group of at least one further antiprotozoal active agent is selected from the group of fluoroquinolone derivatives, artemisinine derivatives (e.g. artemether, artemotil, artesunate, artelinic acid, dihydroartemisinine), chloroquine, proguanil, mefloquine, lumefantrine, quinine, doxycycline, halofantrine, primaquine, sulfadoxine, tetracycline, pyrimethamine, atovaquone, cycloguanil.

In case where more than one active agent is present in the pharmaceutical composition, the pharmaceutical composition may be adapted for allowing simultaneous, separate or sequential administration of the different active agents.

In addition, the present invention provides a method for treating or for the prophylaxis of a disease caused by a parasite, like a protozoa, in particular, of protozoa of the group of *Apicomplexa* or flagellates. The method comprises the step of administering a therapeutically effective amount of a compound according to the present invention. The skilled person is well aware of determining the effective amount, however, for the purpose of the present invention, a therapeutically effective dosage of the compounds according to the present invention may preferably from about 1 to 2000 mg/day preferably from about 10 to 1000 mg/day and further preferred from about 20 to about 500 mg/day, which may be administered in one or multiple doses.

The administration and the method for the treatment or prophylaxis according to the present invention may be effected by any route of administration including oral, parenteral, such as subcutaneous, intravenous, intramuscular, intraperitoneal, intrathecal, transdermal, transmucosal, subdural, nasal, local or topical via iontophoresis, sublingual, by inhalation spray, aerosol or rectally and the like in dosage units formulations optionally comprising conventional pharmaceutically acceptable excipients, diluents or carriers. The method is particularly useful for treating the infection by a parasite and a disease selected from the following:
  a) *Plasmodium* and malaria said parasite being preferably *plasmodium falciparum;*
  b) *Toxoplasma gondii* and toxoplasmosis;
  c) *Eimeria* and coccidiosis;
  d) *Isospora* and isosporiasis/coccidiosis
  e) *Babesia* and babesiosis;
  f) *Cyclospora* and cyclosporiasis;
  g) *Cryptosporidium* and cryptosporidiosis;
  h) *Theileria* and theileriaosis;
  i) *Neospora* and neosporosis;
  j) *Sarcocystis/Hoareosporidium* and sarcocystiosis.

In another embodiment of the method according to the present invention, the method comprises treatment of the subject with sub antiprotozoal dosage together with at least one further antiprotozoal active agent being present in a sub antiprotozoal dosage. Thus, it is possible to avoid any side effects including toxicity of the single substances while maintaining the antiprotozoal activity and efficacy. In addition, it is expected to have a positive effect on the risk of the development of resistance against the active agent. When administering the compound according to the present invention in combination with at least one further compound, administration may be effected simultaneously, separately or sequentially. For example, the pharmaceutical composition containing both antiprotozoal active agents may be a composition wherein both active agents are mixed in advance or may be present separately.

The formulation of the pharmaceutical composition according to the present invention which may be used as defined herein, in particular, in a method according to the present invention may be in a way that the dosage may be an immediate release dosage or a sustained dosage depending on the route of administration.

The following examples are provided to add the understanding of the present invention, the true scope of which is set forth in the appended claims. It is understood that modification can be made in the procedures set forth without departing from spirit of the invention.

Introduction into the Synthesis and Chemical Properties of Bisarylcyclobutenediones The 3,4-bis(indol-3-yl)cyclobut-3-ene-1,2-diones, which are at least unsubstituted at one of two nitrogens, are a subgroup of bisarylcyclobutenediones (1). Several examples of bisarylcyclobutenediones are documented in the literature, however, the class of molecules which is claimed in the present patent application has to our best knowledge not been described or mentioned before. Bisarylcyclobutenediones are derived from squaric acid (2) by the formal replacement of the two hydroxyl groups by aryl or heteroaryl substituents, respectively.

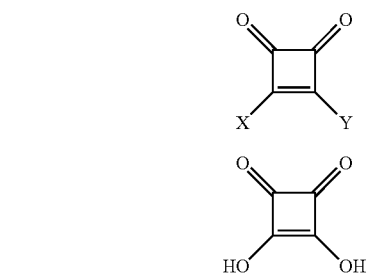

X, Y = aryl or heteroaryl

Diphenylcyclobutenediones can be prepared by Friedel-Crafts-acylation of dichlorocyclobutenedione (squaric acid dichloride) (3) with substituted benzenes, as described for the unsubstituted diphenylcyclobutenedione 4 (B. R. Green, E. W. Neuse, *Synthesis* 1974, 46-47):

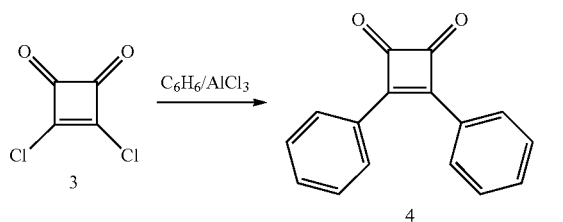 [SMILES: O=c1c(Cl)c(Cl)c1=O ; O=c1c(-c2ccccc2)c(-c2ccccc2)c1=O]

The dipyrrylcyclobutenedione 6 was prepared by condensation of diacetoxycyclobutenedione 5 with 2-methylpyrrole (A. Treibs, K. Jacob, *Liebigs Ann. Chem.* 1966, 699, 153-167):

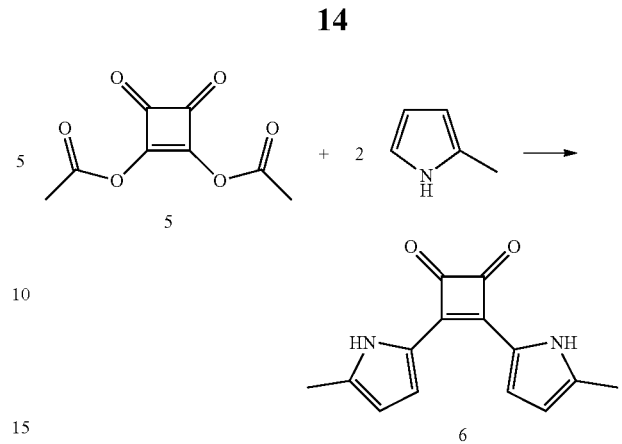

Also cross-coupling-reactions have been employed for the preparation of various substituted diarylcyclobutenediones (Z. Liu et al., *Eur. J. Med. Chem.* 2013, 65, 187-194), for example compound 7:

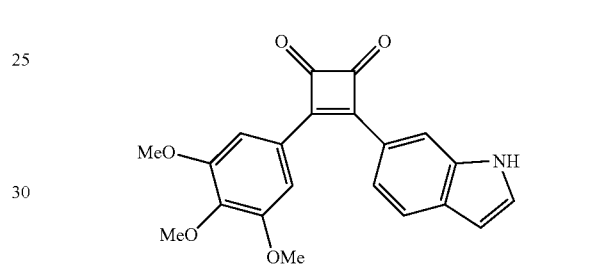

Several of these diarylcyclobutenediones exhibited potent activities against human tumor cell lines (Z. Liu et al., *Eur. J. Med. Chem.* 2013, 65, 187-194).

The bispyrryl- and bisindolylcyclobutenediones 8 and 9 were prepared as potential photochromic dyes (M. Matsuoka et al., *Dyes Pigm.* 1991, 16, 309-315). Of note, in contrast to the compounds according to the present application, compound 9 is substituted at both indole nitrogen atoms.

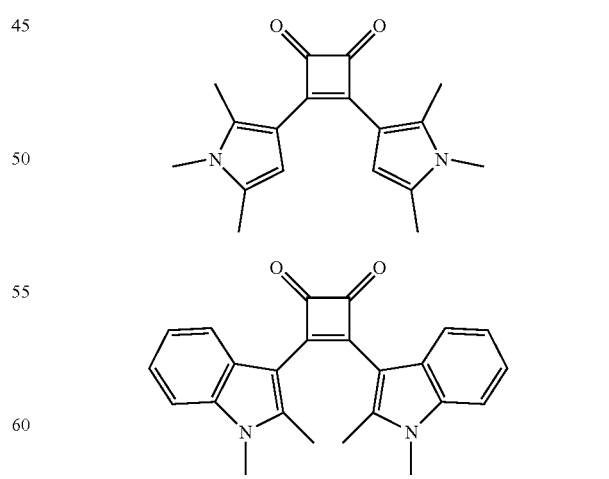

Also 2-phenylindolizine can be acylated by squaric acid dichloride giving the bisindolizin-3-yl-cyclobutenedione 10, which was tested as photosensibilisator (W. Ried, H. Medem, *Synthesis* 1974, 670-671):

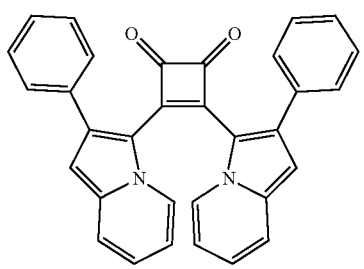

The bis-3-thienylcyclobutenedione 11 was obtained by acylation of squaric acid dichloride. Subsequent Baeyer-Villiger oxidation of 11 gave the target compound 12, which was tested for its photochromic properties (V. Z. Shirinyan et al., Chem. Heterocycl. Compd. 2001, 37, 77-84):

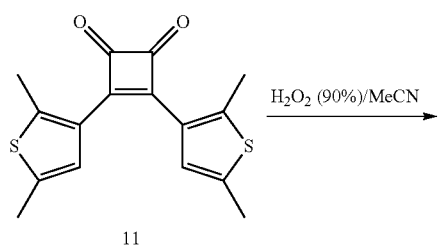

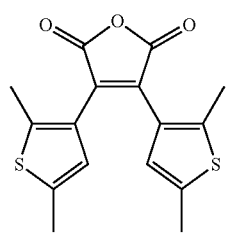

EXAMPLES

General

Starting materials, reagents, and solvents were mainly purchased from Acros Organics (Geel, Belgium), Sigma Aldrich (Steinheim, Germany) and Alfa Aesar (Karlsruhe, Germany). Melting points were determined in open-glass capillaries on an electric variable heater (Electrothermal IA 9100). $^1$H-NMR spectra were recorded on a Bruker Avance DRX-500 (400.1 MHz) and a Bruker Avance II-600 (600.1 MHz), respectively, using DMSO-$d_6$ and CDCl$_3$, respectively, as solvents. Chemical shifts are reported as parts per million (ppm) downfield from tetramethylsilane used as an internal standard. The elemental analyses were recorded on a CE Instruments FlashEA® 1112 Elemental Analyzer. The reactions were monitored by TLC (Macherey-Nagel Polygram SIL G/UV254).

Syntheses of Compounds

3,4-Dichlorocyclobut-3-ene-1,2-dione (Squaric Acid Dichloride)

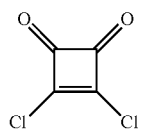

Experimental procedure taken from LUNELLI et al. [B. Lunelli, Tetrahedron Lett. 2007, 3595-3597].

Finely powdered squaric acid (11.4 g, 0.10 mol) was suspended in anhydrous carbon tetrachloride (50 mL). After addition of anhydrous N,N-dimethylformamide (0.400 mL) and oxalyl chloride (18.0 mL, 0.200 mol), the reaction mixture was heated at 50° C. for four hours. After cooling to room temperature, the mixture was filtered, and the filtrate was evaporated under reduced pressure. The resulting oily residue crystallized in the refrigerator. Subsequently, the spontaneously precipitated, light yellow, easily sublimating crystals were separated, washed with petroleum ether and stored in the refrigerator. The product (Yield: 79%) was used without any further purification.

Mp=50-53° C. (53° C. [B. Lunelli, Tetrahedron Lett. 2007, 3595-3597]).

Syntheses of 3-chloro-4-(1H-indol-3-yl)cyclobut-3-ene-1,2-dione Derivatives Method A:

With reference to SCHMIDT et al., the 3-chloro-4-(1H-indol-3-yl)cyclobut-3-ene-1,2-dione derivatives were synthesized as described below: [A. H. Schmidt et al; J. Chem. Soc., Perkin Trans. 1 1996, 495-496].

To squaric acid dichloride (3) (1.51 g, 10.0 mmol) dissolved in dry diethyl ether (25 mL) and cooled to 0° C., a solution of the appropriate indole (12.0 mmol) in the same solvent (25 mL) is added dropwise. The mixture is allowed to warm to room temperature and stirred for twenty-four hours. The resulting precipitate is filtered, washed with diethyl ether and crystallized from chloroform/N,N-dimethylformamide. The product is dried at 110° C. in vacuo.

3-Chloro-4-(1H-indol-3-yl)cyclobut-3-ene-1,2-dione

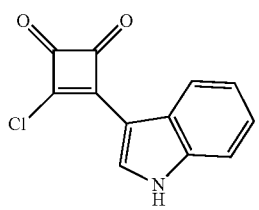 [SMILES: O=c1c(Cl)c(-c2c[nH]c3ccccc23)c1=O]

The compound was synthesized as described in method A; ocher powder (Yield: 67%). $^1$H-NMR (600 MHz, DMSO-$d_6$): δ (ppm)=7.20 (ddd, J=8.1, 7.0, 1.2 Hz, 1H, ArH), 7.22 (ddd, J=8.1, 7.1, 1.3 Hz, 1H, ArH), 7.51 (dt, J=8.1, 1.0 Hz, 1H, ArH), 8.20 (d, J=3.0 Hz, 1H, ArH), 8.30 (ddt, J=7.9, 1.4, 0.8 Hz, 1H, ArH), 12.27 (s, 1H, NH).

Anal. calcd. for $C_{12}H_6ClNO_2$: C, 62.22, H, 2.61, N, 6.05. Found: C, 61.95, H, 2.52, N, 5.82.

3-Chloro-4-(5-methoxy-1H-indol-3-yl)cyclobut-3-ene-1,2-dione

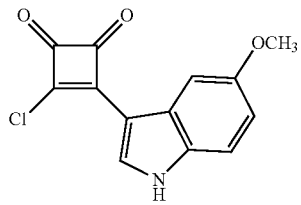 [SMILES: COc1ccc2[nH]cc(-c3c(Cl)c(=O)c3=O)c2c1]

The compound was synthesized as described in method A; green powder (Yield: 74%). $^1$H-NMR (400 MHz, DMSO-$d_6$): δ (ppm)=3.78 (s, 3H, $CH_3$), 6.88 (dd, J=8.8, 2.5 Hz, 1H, ArH), 7.40 (dd, J=8.8, 0.6 Hz, 1H, ArH), 7.84 (d, J=2.5 Hz, 1H, ArH), 8.13 (d, J=3.1 Hz, 1H, ArH), 11.41 (s, 1H, NH).

3-Chloro-4-(1-methyl-1H-indol-3-yl)cyclobut-3-ene-1,2-dione

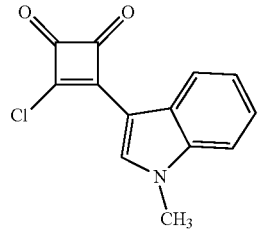 [SMILES: Cn1cc(-c2c(Cl)c(=O)c2=O)c2ccccc21]

The compound was synthesized as described in method A; yellowish powder (Yield: 27%).

$^1$H-NMR (400 MHz, DMSO-$d_6$): δ (ppm)=3.93 (s, 3H, $CH_3$), 7.26 (ddd, J=8.0, 7.1, 1.1 Hz, 1H, ArH), 7.32 (ddd, J=8.2, 7.1, 1.3 Hz, 1H, ArH), 7.57 (dt, J=8.2, 0.9 Hz, 1H, ArH), 8.26 (s, 1H, ArH), 8.32-8.29 (m, 1H, ArH).

3-(5-Bromo-1H-indol-3-yl)-4-chlorcyclobut-3-ene-1,2-dione

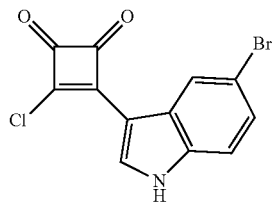 [SMILES: O=c1c(Cl)c(-c2c[nH]c3ccc(Br)cc23)c1=O]

The compound was synthesized as described in method A; ocher powder (Yield: 14%). $^1$H-NMR (400 MHz, DMSO-$d_6$): δ (ppm)=7.37 (dd, J=8.7, 2.0 Hz, 1H, ArH), 7.49 (dd, J=8.6, 0.5 Hz, 1H, ArH), 8.21 (d, J=3.0 Hz, 1H, ArH), 8.49 (d, J=2.0 Hz, 1H, ArH), 12.42 (s, 1H, NH).

3-Chloro-4-(2-methyl-1H-indol-3-yl)cyclobut-3-ene-1,2-dione

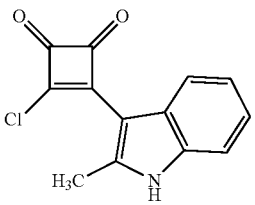 [SMILES: Cc1[nH]c2ccccc2c1-c1c(Cl)c(=O)c1=O]

The compound was synthesized as described in method A; green powder (Yield: 83%). $^1$H-NMR (400 MHz, DMSO-$d_6$): δ (ppm)=2.80 (s, 3H, $CH_3$), 7.12 (dtd, J=16.0, 7.2, 1.4 Hz, 2H, ArH), 7.35 (dd, J=7.2, 1.6 Hz, 1H, ArH), 8.21 (dd, J=7.4, 1.5 Hz, 1H, ArH), 12.12 (s, 1H, NH).

3-Chloro-4-(2-phenyl-1H-indol-3-yl)cyclobut-3-ene-1,2-dione

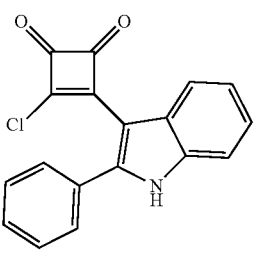 [SMILES: O=c1c(Cl)c(-c2c(-c3ccccc3)[nH]c3ccccc23)c1=O]

The compound was synthesized as described in method A and was purified by column chromatography on silica gel using ethyl acetate/petroleum ether (1/1); orange powder (Yield: 65%).

$^1$H-NMR (400 MHz, DMSO-$d_6$): δ (ppm)=7.16 (ddd, J=8.1, 7.1, 1.1 Hz, 1H, ArH), 7.23 (ddd, J=8.1, 7.1, 1.3 Hz, 1H, ArH), 7.40-7.50 (m, 4H, ArH), 7.54-7.62 (m, 2H, ArH), 8.06 (dd, J=7.7, 1.0 Hz, 1H, ArH), 12.30 (s, 1H, NH).

Syntheses of 3-chloro-4-(1H-pyrrolo[2,3-b]pyridin-3-yl)cyclobut-3-ene-1,2-dione Derivatives Method B:

With reference to ZHANG et al. 3-Chloro-4-(1H-pyrrolo[2,3-b]pyridin-3-yl)cyclobut-3-ene-1,2-dione derivatives were synthesized as described below: [Z. Zhang et al., J. Org. Chem. 2002, 6226-7].

To the stirred solution of an appropriate 7-aza-1H-indole (2.00 mmol) in dry dichloromethane (20 mL), precooled to 0° C., anhydrous aluminium chloride (1.33 g, 10.0 mmol) is added. After stirring for 1 h at room temperature, a solution of 3,4-dichlorocyclobut-3-ene-1,2-dione (squaric acid dichloride, 0.900 g, 5.96 mmol) in the same solvent (20 mL) is added dropwise, and the resulting mixture is stirred for further sixteen hours at room temperature. The precipitate is separated and washed with water. The resulting solid is dried at 100° C. in vacuo and used without further purification.

3-Chloro-4-(1H-pyrrolo[2,3-b]pyridin-3-yl)cyclobut-3-ene-1,2-dione

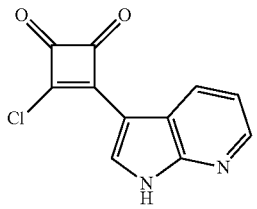 [SMILES: O=c1c(Cl)c(-c2c[nH]c3ncccc23)c1=O]

The compound was synthesized as described in method B; pink powder (Yield: 90%). $^1$H-NMR (400 MHz, DMSO-$d_6$): δ (ppm)=7.40 (dd, J=8.0, 5.0 Hz, 1H, ArH), 8.21 (bs, 1H, ArH), 8.42 (dd, J=5.1, 1.5 Hz, 1H, ArH), 8.91 (dd, J=8.0, 1.5 Hz, 1H, ArH), 12.91 (bs, 1H, NH).

3-(5-Bromo-1H-pyrrolo[2,3-b]pyridin-3-yl)-4-chlorocyclobut-3-ene-1,2-dione

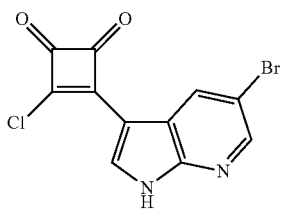 [SMILES: O=c1c(Cl)c(-c2c[nH]c3ncc(Br)cc23)c1=O]

The compound was synthesized as described in method B; red powder (Yield: 75%) $^1$H-NMR (600 MHz, DMSO-$d_6$): δ (ppm)=8.21 (d, J=2.9 Hz, 1H, ArH), 8.41 (d, J=2.3 Hz, 1H, ArH), 8.83 (dd, J=2.3, 0.5 Hz, 1H, ArH), 12.85 (bs, 1H, NH).

Syntheses of N-unsubstituted 3,4-bis(indol-3-yl)cyclobut-3-ene-1,2-diones

Method C:

With reference to GREEN et al. [B. R. Green, B. R. et al., Synthesis 1974, 46-7] and MATSUOKA et al. [M. Matsuoka et al., Dyes Pigm. 1991, 309-315], the N-unsubstituted 3,4-bis (indol-3-yl)cyclobut-3-ene-1,2-diones were synthesized as described below: To a suspension of 3,4-dichlorocyclobut-3-ene-1,2-dione (squaric acid dichloride, 0.300 g, 2.00 mmol) and anhydrous aluminium chloride (800 mg, 6.00 mmol) in dry dichloromethane, the appropriate indole (4.00 mmol) is added. The mixture is stirred for twenty-four to thirty hours at room temperature with moisture protection. Subsequently, the reaction suspension is stirred in a mixture of water (50 mL) and five drops of 37% aqueous hydrochloric acid. The resulting precipitate is separated and washed with water. After drying, the residue is dissolved in acetone (10 mL) and eluated through a column of acidic aluminium oxide with acetone. The yellow or tawny fraction is collected and evaporated under reduced pressure. The solid residue is crystallized from an appropriate solvent or purified by silica gel column chromatography. The resulting product is dried at 80-90° C. in vacuo.

Method D:

With reference to GREEN et al. [B. R. Green et al., Synthesis 1974, 46-7] and MATSUOKA et al. [M. Matsuoka et al; Dyes Pigm. 1991, 309-315], the N-unsubstituted 3,4-bis (indol-3-yl)cyclobut-3-ene-1,2-diones were synthesized as described below:

To the stirred suspension of an appropriate 3-chloro-4-(1H-indol-3-yl)cyclobut-3-ene-1,2-dione derivative (1.00 mmol) and anhydrous aluminium chloride (400 mg, 3.00 mmol) in dry dichloromethane (20 mL), precooled to 0° C., a solution of an appropriate indole (1.50 mmol) in the same solvent (10 mL) is added dropwise. The reaction mixture is allowed to warm to room temperature. After stirring for twenty-four to forty-eight hours at room temperature with moisture protection, the suspension is added to a mixture of water (50 mL) and 5 drops of 37% aqueous hydrochloric acid. The resulting precipitate is filtered and washed with water. After drying, the solid is eluated through a column of acidic aluminium oxide using acetone. The yellow or tawny eluent is collected and evaporated under reduced pressure. Subsequently, the solid residue is crystallized from the given solvent or purified by silica gel column chromatography using ethyl acetate/petroleum ether. The resulting product is dried at 80-90° C. in vacuo.

Method E:

With reference to GREEN et al. [B. R. Green et al., Synthesis 1974, 46-7] the N-unsubstituted 3,4-bis(indol-3-yl) cyclobut-3-ene-1,2-diones were synthesized as described below:

To the stirred suspension of an appropriate 3-chloro-4-(1H-indol-3-yl)cyclobut-3-ene-1,2-dione (1.00 mmol) derivative and anhydrous aluminium chloride (400 mg, 3.00 mmol) in dry dichloromethane (20 mL), precooled to 0° C., a solution of an appropriate indole (1.50 mmol) in the same solvent (10 mL) is added dropwise. The reaction mixture is allowed to warm to room temperature. After stirring for twenty-four hours at room temperature with moisture protection, the suspension is added to a mixture of water (50 mL) and 5 drops 37% aqueous hydrochloric acid. The resulting precipitate is filtered and washed with water. After drying, the residue is dissolved in ethyl acetate (30 mL) and washed with water (2×50 mL) and brine (50 mL). The aqueous layer is extracted with ethyl acetate (3×20 mL). After drying the combined organic layers with anhydrous sodium sulfate, the solvent is removed under reduced pressure. Subsequently, the resulting residue is crystallized from a suitable solvent and dried at 80-90° C. in vacuo.

Method F:

With reference to Faul et al. the N-unsubstituted 3,4-bis (indol-3-yl)cyclobut-3-ene-1,2-dione derivatives were synthesized as described below: [M. M. Faul et al; Synthesis 1995, 1511-1516].

To a stirred solution of an appropriate indole (5 mmol) in anhydrous toluene (8.35 mL) is added ethyl magnesium bromide (3.0 M in diethyl ether, 1.67 mL) under nitrogen. After heating to 60° C. for one hour, a solution of squaric acid dichloride in dry tetrahydrofurane (1.64 mL) is added slowly. Subsequently, the reaction mixture is refluxed for four hours under nitrogen, cooled to room temperature and diluted with ethyl acetate (25 mL). The organic layer is washed with 1 M aqueous hydrochloric acid (15 mL), water (2×15 mL), brine (15 mL) and dried with anhydrous sodium sulfate. After evaporation under reduced pressure, the product is crystallized from the given solvent and then dried at 80-90° C. in vacuo.

Method G:

With reference to Faul et al. the N-unsubstituted 3,4-bis (indol-3-yl)cyclobut-3-ene-1,2-dione derivatives were synthesized as described below [M. M. Faul et al; Synthesis 1995, 1511-1516]:

To a stirred solution of an appropriate indole (3 mmol) in anhydrous toluene (8.35 mL) is added ethyl magnesium bromide (3.0 M in diethyl ether, 1.67 mL) under nitrogen. After heating to 60° C. for one hour, a suspension of an appropriate 3-chloro-4-indol-3-ylcyclobut-3-ene-1,2-dione derivative in a mixture of dry toluene/diethyl ether/tetrahydrofurane (8.35 mL/1 mL/2.67 mL) is added slowly. Subsequently, the reaction mixture is refluxed for four hours under nitrogen, cooled to room temperature and diluted with ethyl acetate (25 mL). The organic layer is washed with 1 M aqueous hydrochloric acid (15 mL), water (2×15 mL), brine (15 mL) and dried with anhydrous sodium sulfate. After evaporation under reduced pressure, the product is crystallized from the given solvent and then dried at 80-90° C. in vacuo.

Example 1: 3,4-Bis(1H-indol-3-yl)cyclobut-3-ene-1,2-dione (KuHL043)

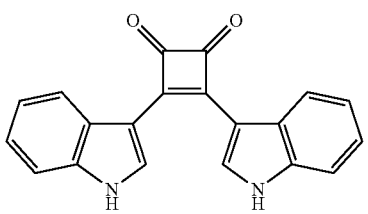

(II)

The compound was synthesized as described in method G from 3-chloro-4-(1H-indol-3-yl)cyclobut-3-ene-1,2-dione (0.262 g, 1.13 mmol) and 1H-indole (0.360 g, 3.08 mmol). Crystallization from ethanol/toluene yielded a yellow powder (Yield: 66%).

$^1$H-NMR (400 MHz, DMSO-$d_6$): δ (ppm)=7.17 (ddd, J=8.1, 7.1, 1.1 Hz, 2H), 7.28 (ddd, J=8.2, 7.1, 1.2 Hz, 2H), 7.58 (dt, J=8.2, 0.9 Hz, 2H), 7.93 (dt, J=8.0, 0.9 Hz, 2H), 8.26 (d, J=3.0 Hz, 2H), 12.44 (s, 2H, NH).

Anal. calcd. for $C_{20}H_{12}N_2O_2$ [312.33]: C, 76.91, H, 3.87, N, 8.97. Found: C, 76.41, H, 3.70, N, 8.87.

MS (EI): m/z (%)=312.1 [M]$^+$ (35), 256.1 [M−56]$^+$ (100).

Example 2: 3,4-Bis(5-methoxy-1H-indol-3-yl)cyclobut-3-ene-1,2-dione (KuHL048)

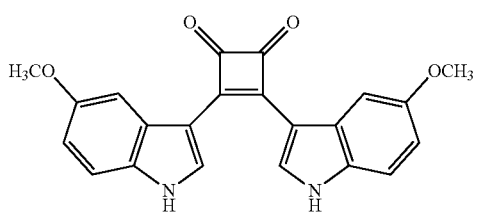 [SMILES: COc1ccc2[nH]cc(-c3c(-c4c[nH]c5ccc(OC)cc45)c(=O)c3=O)c2c1]

The compound was synthesized as described in method D from 3-chloro-4-(5-methoxy-1H-indol-3-yl)cyclobut-3-ene-1,2-dione (0.267 g, 1.02 mmol) and 5-methoxy-1H-indole (0.315 g, 2.14 mmol); yellow powder (Yield: 12%).

$^1$H-NMR (600 MHz, DMSO-$d_6$): δ (ppm)=3.51 (s, 6H, $CH_3$), 6.88 (ddd, J=8.8, 2.5, 0.3 Hz, 2H, ArH), 7.31-7.35 (m, 2H, ArH), 7.46 (dd, J=8.8, 0.5 Hz, 2H, ArH), 8.20 (d, J=0.4 Hz, 2H, ArH), 12.32 (s, 2H, NH).

Example 3: 3,4-Bis(2-phenyl-1H-indol-3-yl)cyclobut-3-ene-1,2-dione (KuHL009)

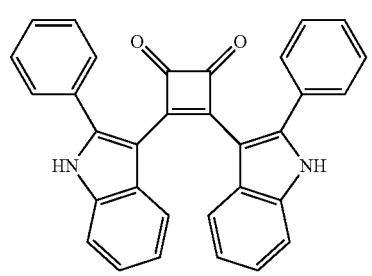

(III)

The compound was synthesized as described in method C and purified by silica gel column chromatography using toluene/ethyl acetate (1/1) and crystallization from ethyl acetate; orange powder (Yield: 12%).

$^1$H-NMR (400 MHz, DMSO-$d_6$): δ (ppm)=7.01 (ddd, J=8.1, 7.1, 1.0 Hz, 2H), 7.05-7.22 (m, 8H), 7.26-7.32 (m, 4H), 7.36 (dt, J=8.1, 0.9 Hz, 2H), 7.43 (d, J=8.0 Hz, 2H), 12.12 (s, 2H).

Example 4: 3,4-Bis(2-methyl-1H-indol-3-yl)cyclobut-3-ene-1,2-dione (KuHL012)

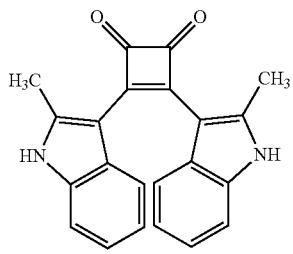

The compound was synthesized as described in method C and purified by silica gel column chromatography using petroleum ether/ethyl acetate (1/1); yellow powder (Yield: 6%). $^1$H-NMR (400 MHz, DMSO-$d_6$): δ (ppm)=2.40 (s, 6H, $CH_3$), 6.90 (ddd, J=8.0, 7.1, 1.0 Hz, 2H, ArH), 7.10 (ddd, J=8.1, 7.1, 1.1 Hz, 2H, ArH), 7.20-7.25 (m, 2H, ArH), 7.39 (dt, J=8.1, 0.9 Hz, 2H, ArH), 12.12 (s, 2H, NH).

Example 5: 3-(5-Chloro-1H-indol-3-yl)-4-(1H-indol-3-yl)cyclobut-3-ene-1,2-dione (KuHL118)

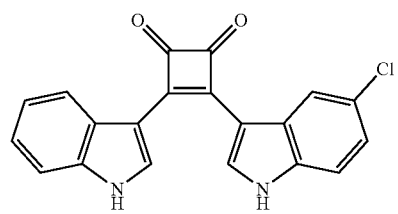 [SMILES: O=c1c(-c2c[nH]c3ccccc23)c(-c2c[nH]c3ccc(Cl)cc23)c1=O]

The compound was synthesized as described in method D from 3-chloro-4-(1H-indol-3-yl)cyclobut-3-ene-1,2-dione (0.241 g, 1.04 mmol) and 5-chloro-1H-indole (0.227 g, 1.50 mmol). Boiling in ethanol/toluene yielded a yellowish powder (Yield: 38%). ¹H-NMR (600 MHz, DMSO-d$_6$): δ (ppm) =7.20 (ddd, J=8.1, 7.0, 1.1 Hz, 1H, ArH), 7.27-7.33 (m, 2H, ArH), 7.57-7.63 (m, 2H, ArH), 7.91 (ddt, J=8.1, 1.4, 0.7 Hz, 1H, ArH), 8.08 (dt, J=2.1, 0.6 Hz, 1H, ArH), 8.28 (d, J=3.1 Hz, 1H, ArH), 8.35 (d, J=3.1 Hz, 1H, ArH), 12.50 (d, J=3.1 Hz, 1H, NH), 12.58 (d, J=3.0 Hz, 1H, NH).

Example 6: 3-(5-Bromo-1H-indol-3-yl)-4-(1H-indol-3-yl)cyclobut-3-ene-1,2-dione (KuHL037)

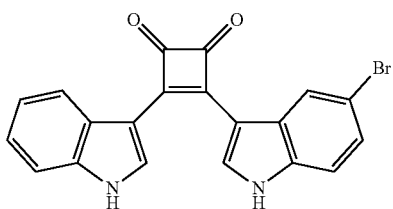

(IV)

The compound was synthesized as described in method D from 3-chloro-4-(1H-indol-3-yl)cyclobut-3-ene-1,2-dione (0.256 g, 1.11 mmol) and 5-bromo-1H-indole (0.392 g, 2.00 mmol); tawny powder (Yield: 38%).

¹H-NMR (400 MHz, DMSO-d$_6$): δ (ppm)=7.19 (ddd, J=8.1, 7.1, 1.1 Hz, 1H, ArH), 7.30 (ddd, J=8.2, 7.1, 1.2 Hz, 1H, ArH), 7.41 (dd, J=8.6, 2.0 Hz, 1H, ArH), 7.51-7.63 (m, 2H, ArH), 7.90 (ddt, J=8.0, 1.2, 0.6 Hz, 1H, ArH), 8.22 (d, J=2.0 Hz, 1H, ArH), 8.26 (d, J=3.0 Hz, 1H, ArH), 8.35 (d, J=3.1 Hz, 1H, ArH), 12.50 (d, J=3.2 Hz, 1H, NH), 12.57 (d, J=3.3 Hz, 1H, NH).

Example 7: 3-(1H-indol-3-yl)-4-(5-iodo-1H-indol-3-yl)cyclobut-3-ene-1,2-dione (KuHL117)

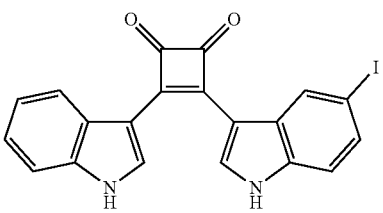 [SMILES: O=c1c(-c2c[nH]c3ccccc23)c(-c2c[nH]c3ccc(I)cc23)c1=O]

The compound was synthesized as described in method D from 3-chloro-4-(1H-indol-3-yl)cyclobut-3-ene-1,2-dione (0.234 g, 1.01 mmol) and 5-iodo-1H-indole (0.360 g, 1.48 mmol). Crystallization from ethyl acetate yielded a yellow powder (Yield: 36%). ¹H-NMR (600 MHz, DMSO-d$_6$): δ (ppm)=7.19 (ddd, J=8.0, 7.0, 1.0 Hz, 1H, ArH), 7.30 (ddd, J=8.2, 7.1, 1.2 Hz, 1H, ArH), 7.43 (dd, J=8.5, 0.6 Hz, 1H, ArH), 7.53-7.62 (m, 2H, ArH), 7.90 (dt, J=8.0, 1.0 Hz, 1H, ArH), 8.22 (s, 1H), 8.33 (s, 1H, ArH), 8.39 (dd, J=1.7, 0.5 Hz, 1H, ArH), 12.53 (s, 2H, NH).

Example 8: 3-[2-(1H-Indol-3-yl)-3,4-dioxocyclobut-1-ene-1-yl]-1H-indol-5-carbonitrile (KuHL122)

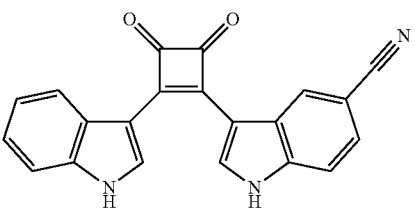 [SMILES: N#Cc1ccc2[nH]cc(-c3c(-c4c[nH]c5ccccc45)c(=O)c3=O)c2c1]

The compound was synthesized as described in method D from 3-chloro-4-(1H-indol-3-yl)cyclobut-3-ene-1,2-dione (0.265 g, 1.14 mmol) and 1H-indole-5-carbonitrile (0.213 g, 1.50 mmol). Crystallization from ethanol/toluene yielded a yellow powder (Yield: 52%). ¹H-NMR (600 MHz, DMSO-d$_6$): δ (ppm)=7.19 (ddd, J=8.1, 7.1, 1.1 Hz, 1H, ArH), 7.30 (ddd, J=8.2, 7.0, 1.1 Hz, 1H, ArH), 7.60 (dt, J=8.1, 0.9 Hz, 1H, ArH), 7.65 (dd, J=8.5, 1.6 Hz, 1H, ArH), 7.75 (dd, J=8.5, 0.7 Hz, 1H, ArH), 7.88 (ddt, J=8.0, 1.3, 0.7 Hz, 1H, ArH), 8.39 (d, J=3.0 Hz, 1H, ArH), 8.42 (d, J=3.1 Hz, 1H, ArH), 8.47 (dt, J=1.5, 0.7 Hz, 1H, ArH), 12.54-12.58 (m, 1H, NH), 12.82-12.86 (m, 1H, NH).

Example 9: 3-(1H-Indol-3-yl)-4-(2-phenyl-1H-indol-3-yl)cyclobut-3-ene-1,2-dione (KuHL044)

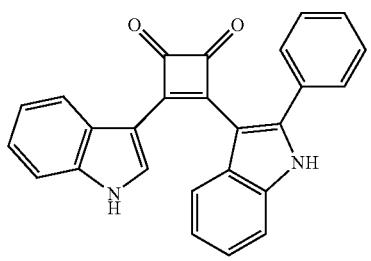

(V)

The compound was synthesized as described in method D from 3-chloro-4-(1H-indol-3-yl)cyclobut-3-ene-1,2-dione (0.238 g, 1.03 mmol) and 2-phenyl-1H-indole (0.388 g, 2.01 mmol); yellow powder (Yield: 70%).

¹H-NMR (400 MHz, DMSO-d$_6$): δ (ppm)=6.99-7.11 (m, 2H, ArH), 7.12-7.35 (m, 5H, ArH), 7.38-7.48 (m, 2H, ArH), 7.48-7.60 (m, 3H, ArH), 7.75-7.81 (m, 1H, ArH), 7.85 (d, J=7.9 Hz, 1H, ArH), 12.24 (d, J=3.0 Hz, 1H, NH), 12.44 (s, 1H, NH).

Example 10: 3-(1H-Indol-3-yl)-4-(5-methoxy-1H-indol-3-yl)cyclobut-3-ene-1,2-dione (KuHL049)

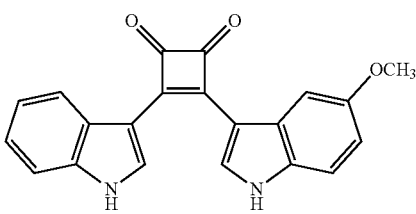 [SMILES: COc1ccc2[nH]cc(-c3c(-c4c[nH]c5ccccc45)c(=O)c3=O)c2c1]

The compound was synthesized as described in method D from 3-chloro-4-(1H-indol-3-yl)cyclobut-3-ene-1,2-dione (0.240 g, 1.04 mmol) and 5-methoxy-1H-indole (0.322 g, 2.19 mmol); yellow powder (Yield: 11%). ¹H-NMR (600 MHz, DMSO-d₆): δ (ppm)=3.53 (s, 3H, CH₃), 6.89 (dd, J=8.8, 2.5 Hz, 1H, ArH), 7.15 (ddd, J=8.0, 7.0, 1.0 Hz, 1H, ArH), 7.27 (ddd, J=8.2, 7.1, 1.1 Hz, 1H, ArH), 7.31-7.34 (m, 1H, ArH), 7.47 (dd, J=8.8, 0.5 Hz, 1H, ArH), 7.58 (dt, J=8.1, 0.9 Hz, 1H, ArH), 7.91 (dt, J=8.0, 0.9 Hz, 1H, ArH), 8.21 (s, 1H, ArH), 8.25 (s, 1H, ArH), 12.38 (s, 2H, NH).

Example 11: 3-(1H-Indol-3-yl)-4-(2-methyl-1H-indol-3-yl)cyclobut-3-ene-1,2-dione (KuHL025)

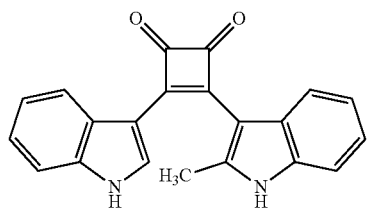 [SMILES: Cc1[nH]c2ccccc2c1-c1c(-c2c[nH]c3ccccc23)c(=O)c1=O]

The compound was synthesized as described in method D from 3-chloro-4-(2-methyl-1H-indol-3-yl)cyclobut-3-ene-1,2-dione (0.233 g, 0.95 mmol) and 1H-indole (0.233 g, 1.99 mmol); yellow powder (Yield: 17%). ¹H-NMR (600 MHz, DMSO-d₆): δ (ppm)=2.55 (s, 3H), 6.98 (ddd, J=7.9, 7.1, 1.0 Hz, 1H), 7.08 (ddd, J=8.0, 7.1, 1.0 Hz, 1H), 7.14-7.18 (m, 2H), 7.23 (ddd, J=8.2, 7.1, 1.1 Hz, 1H), 7.44-7.47 (m, 1H), 7.53 (dt, J=8.1, 0.9 Hz, 1H), 7.84 (d, J=8.1 Hz, 1H), 7.91 (s, 1H), 12.17 (s, 1H), 12.38 (s, 1H).

Example 12: 3-(1H-Indol-3-yl)-4-(1-methyl-1H-indol-3-yl)cyclobut-3-ene-1,2-dione (KuHL032)

(VI)

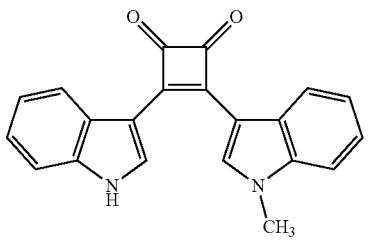

The compound was synthesized as described in method D from 3-chloro-4-(1H-indol-3-yl)cyclobut-3-ene-1,2-dione (0.237 g, 1.02 mmol) and 1-methyl-1H-indole (0.274 mL, 2.19 mmol); yellow powder (Yield: 26%).

¹H-NMR (400 MHz, DMSO-d₆): δ (ppm)=3.98 (s, 3H, CH₃), 7.13-7.40 (m, 4H, ArH), 7.62 (ddt, J=29.0, 8.2, 0.9 Hz, 2H, ArH), 7.89-8.03 (m, 2H, ArH), 8.24-8.30 (m, 1H, ArH), 8.35 (s, 1H, ArH), 12.44 (s, 1H, NH).

Example 13: 3-(5-Fluoro-1H-indol-3-yl)-4-(5-methoxy-1H-indol-3-yl)cyclobut-3-ene-1,2-dione (KuHL113)

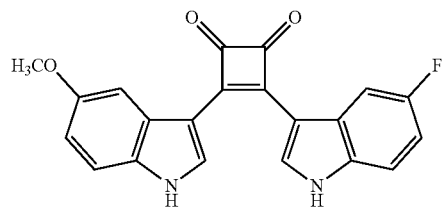 [SMILES: COc1ccc2[nH]cc(-c3c(-c4c[nH]c5ccc(F)cc45)c(=O)c3=O)c2c1]

The compound was synthesized as described in method D from 3-chloro-4-(5-methoxy-1H-indol-3-yl)cyclobut-3-ene-1,2-dione (0.260 g, 1.00 mmol) and 5-fluoro-1H-indole (0.201 g, 1.49 mmol). Crystallization from ethanol/N,N'-dimethylformamide without prior column chromatography yielded a tawny powder (Yield: 51%). ¹H-NMR (600 MHz, DMSO-d₆): δ (ppm)=3.58 (s, 3H, OCH₃), 6.91 (dd, J=8.8, 2.5 Hz, 1H, ArH), 7.14 (td, J=9.1, 2.6 Hz, 1H, ArH), 7.31-7.37 (m, 1H, ArH), 7.48 (dd, J=8.8, 0.5 Hz, 1H, ArH), 7.59 (ddd, J=8.8, 4.7, 0.5 Hz, 1H, ArH), 7.75 (dd, J=10.1, 2.6 Hz, 1H, ArH), 8.24 (d, J=3.1 Hz, 1H, ArH), 8.31 (d, J=3.2 Hz, 1H, ArH), 12.39 (d, J=3.3 Hz, 1H, NH), 12.50 (d, J=3.1 Hz, 1H, NH).

Example 14: 3-(5-Chloro-1H-indol-3-yl)-4-(5-methoxy-1H-indol-3-yl)cyclobut-3-ene-1,2-dione (KuHL102)

(VII)

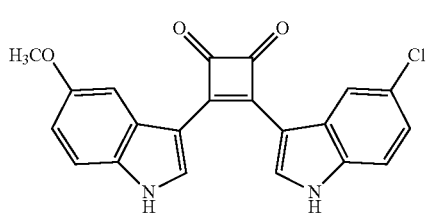

The compound was synthesized as described in method D from 3-chloro-4-(5-methoxy-1H-indol-3-yl)cyclobut-3-ene-1,2-dione (0.262 g, 1.00 mmol) and 5-chloro-1H-indole (0.220 g, 1.45 mmol). Crystallization from ethanol/toluene without prior column chromatography yielded a yellow powder (Yield: 43%).

¹H-NMR (400 MHz, DMSO-d₆): δ (ppm)=3.59 (s, 3H, O—CH₃), 6.93 (dd, J=8.8, 2.5 Hz, 1H, ArH), 7.26-7.35 (m, 2H, ArH), 7.50 (d, J=8.8 Hz, 1H, ArH), 7.61 (dd, J=8.6, 0.5 Hz, 1H, ArH), 8.07 (d, J=2.1 Hz, 1H, ArH), 8.24 (d, J=3.1 Hz, 1H, ArH), 8.33 (d, J=3.2 Hz, 1H, ArH), 12.41 (d, J=3.1 Hz, 1H, NH), 12.55 (d, J=3.1 Hz, 1H, NH).

Example 15: 3-(5-Bromo-1H-indol-3-yl)-4-(5-methoxy-1H-indol-3-yl)cyclobut-3-ene-1,2-dione (KuHL047)

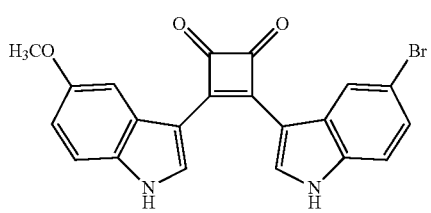

(VIII)

The compound was synthesized as described in method G from 3-chloro-4-(5-methoxy-1H-indol-3-yl)cyclobut-3-ene-1,2-dione (0.262 g, 1.00 mmol) and 5-bromo-1H-indole (0.585 g, 2.98 mmol). Crystallization from petroleum ether/ethyl acetate yielded an orange powder (Yield: 20%).

$^1$H-NMR (600 MHz, DMSO-$d_6$): δ (ppm)=3.58 (s, 3H, CH$_3$), 6.92 (ddd, J=8.8, 2.5, 0.4 Hz, 1H, ArH), 7.28-7.34 (m, 1H, ArH), 7.40 (dd, J=8.6, 2.0 Hz, 1H, ArH), 7.48 (dd, J=8.8, 0.5 Hz, 1H, ArH), 7.55 (dd, J=8.6, 0.5 Hz, 1H, ArH), 8.19-8.23 (m, 2H, ArH), 8.32 (d, J=0.4 Hz, 1H, ArH), 12.45 (s, 2H, NH).

Example 16: 3-(5-Iodo-1H-indol-3-yl)-4-(5-methoxy-1H-indol-3-yl)cyclobut-3-ene-1,2-dione (KuHL101)

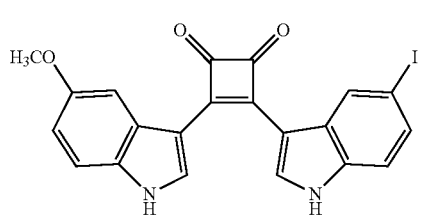

(IX)

The compound was synthesized as described in method D from 3-chloro-4-(5-methoxy-1H-indol-3-yl)cyclobut-3-ene-1,2-dione (0.262 g, 1.00 mmol) and 5-iodo-1H-indole (0.362 g, 1.45 mmol). Crystallization from ethanol/toluene without prior column chromatography yielded a tawny powder (Yield: 43%).

$^1$H-NMR (400 MHz, DMSO-$d_6$): δ (ppm)=3.57 (s, 3H, O—CH$_3$), 6.93 (dd, J=8.8, 2.5 Hz, 1H, ArH), 7.30 (d, J=2.5 Hz, 1H, ArH), 7.44 (dd, J=8.6, 0.6 Hz, 1H, ArH), 7.47-7.60 (m, 2H, ArH), 8.17 (d, J=3.0 Hz, 1H), 8.31 (d, J=3.2 Hz, 1H, ArH), 8.37 (d, J=1.7 Hz, 1H, ArH), 12.40 (d, J=3.2 Hz, 1H, NH), 12.52 (d, J=3.0 Hz, 1H, NH).

Example 17: 3-[2-(5-Methoxy-1H-indol-3-yl)-3,4-dioxocyclobut-1-ene-1-yl]-1H-indol-5-carbonitrile (KuHL103)

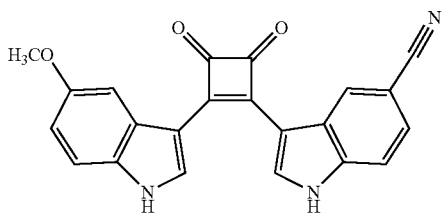 [SMILES: COc1ccc2[nH]cc(-c3c(-c4c[nH]c5ccc(C#N)cc45)c(=O)c3=O)c2c1]

The compound was synthesized as described in method D from 3-chloro-4-(5-methoxy-1H-indol-3-yl)cyclobut-3-ene-1,2-dione (0.258 g, 1.00 mmol) and 1H-indol-5-carbonitrile (0.220 g, 1.55 mmol). Crystallization from ethanol/toluene without prior column chromatography yielded a yellow powder (Yield: 51%). $^1$H-NMR (400 MHz, DMSO-$d_6$): δ (ppm)=3.58 (s, 3H, O—CH$_3$), 6.94 (dd, J=8.8, 2.5 Hz, 1H, ArH), 7.28 (d, J=2.5 Hz, 1H, ArH), 7.45-7.55 (m, 1H, ArH), 7.65 (dd, J=8.5, 1.6 Hz, 1H, ArH), 7.77 (dd, J=8.4, 0.8 Hz, 1H, ArH), 8.37 (dd, J=20.9, 3.1 Hz, 2H, ArH), 8.47 (dd, J=1.5, 0.7 Hz, 1H, ArH), 12.47 (d, J=3.2 Hz, 1H, NH), 12.82 (d, J=2.9 Hz, 1H, NH).

Example 18: 3-[5-(Benzyloxy)-1H-indol-3-yl]-4-(5-methoxy-1H-indol-3-yl)cyclobut-3-ene-1,2-dione (KuHL136)

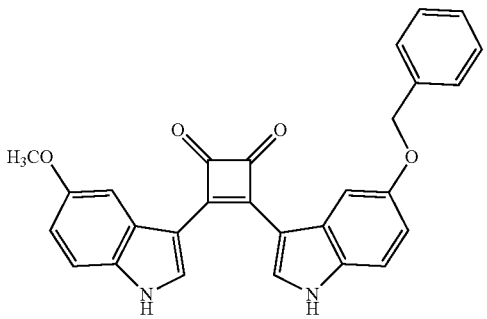 [SMILES: COc1ccc2[nH]cc(-c3c(-c4c[nH]c5ccc(OCc6ccccc6)cc45)c(=O)c3=O)c2c1]

The compound was synthesized as described in method G from 3-chloro-4-(5-methoxy-1H-indol-3-yl)cyclobut-3-ene-1,2-dione (0.274 g, 1.05 mmol) and 5-(benzyloxy)-1H-indole (0.670 g, 3.00 mmol). Crystallization from petroleum ether/ethyl acetate yielded an orange powder (Yield: 52%). $^1$H-NMR (600 MHz, DMSO-$d_6$): δ (ppm)=3.47 (s, 3H, O—CH$_3$), 4.71 (s, 2H, O—CH$_2$), 6.92 (ddd, J=27.7, 8.8, 2.5 Hz, 2H, ArH), 7.23-7.36 (m, 7H, ArH), 7.47 (dd, J=11.3, 8.8 Hz, 2H, ArH), 8.22 (s, 2H, ArH), 12.33 (s, 2H, NH).

Example 19: 3-(5-Methoxy-1H-indol-3-yl)-4-(2-phenyl-1H-indol-3-yl)cyclobut-3-ene-1,2-dione (KuHL058)

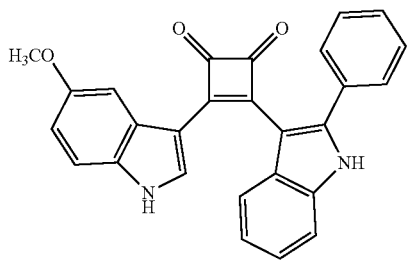 [SMILES: COc1ccc2[nH]cc(-c3c(-c4c(-c5ccccc5)[nH]c5ccccc45)c(=O)c3=O)c2c1]

The compound was synthesized as described in method D from 3-chloro-4-(5-methoxy-1H-indol-3-yl)cyclobut-3-ene-1,2-dione (0.225 g, 0.86 mmol) and 2-phenyl-1H-indole (0.272 g, 1.42 mmol). Crystallization from ethanol/toluene yielded a yellow-orange powder (Yield: 17%). $^1$H-NMR (600 MHz, DMSO-d$_6$): δ (ppm)=3.32 (s, 3H, O—CH$_3$), 6.75 (dd, J=8.8, 2.5 Hz, 1H), 7.03 (ddd, J=8.0, 6.9, 1.0 Hz, 1H, ArH), 7.21-7.36 (m, 6H, ArH), 7.38-7.43 (m, 1H, ArH), 7.53-7.62 (m, 4H, ArH), 12.22 (s, 1H, NH), 12.42 (s, 1H. NH).

Example 20: 3-(5-Methoxy-1H-indol-3-yl)-4-(2-methyl-1H-indol-3-yl)cyclobut-3-en-1,2-dione (KuHL018)

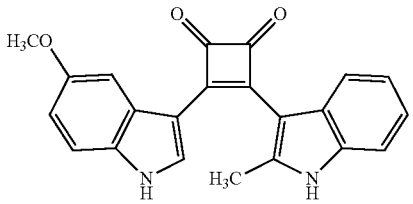 [SMILES: COc1ccc2[nH]cc(-c3c(-c4c(C)[nH]c5ccccc45)c(=O)c3=O)c2c1]

The compound was synthesized as described in method D from 3-chloro-4-(2-methyl-1H-indol-3-yl)cyclobut-3-ene-1,2-dione (0.257 g, 1.05 mmol) and 5-methoxy-1H-indole (0.149 g, 1.01 mmol). Purification via column chromatography using petroleum ether/ethyl acetate and subsequent crystallization from ethanol/toluene yielded a yellow powder (Yield: 20%). $^1$H-NMR (600 MHz, DMSO-d$_6$): δ (ppm)= 2.57 (s, 3H), 3.32 (s, 3H), 6.81 (dd, J=8.8, 2.5 Hz, 1H), 6.94 (ddd, J=8.0, 7.1, 1.0 Hz, 1H), 7.10-7.19 (m, 3H), 7.38-7.46 (m, 2H), 8.00 (s, 1H), 12.13 (s, 1H), 12.29 (s, 1H).

Example 21: 3-(5-Methoxy-1H-indol-3-yl)-4-(1-methyl-1H-indol-3-yl)cyclobut-3-ene-1,2-dione (KuHL057)

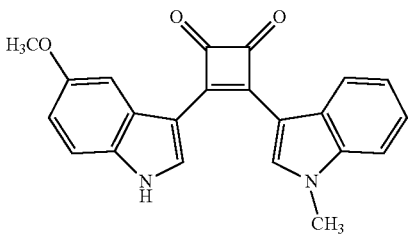 [SMILES: COc1ccc2[nH]cc(-c3c(-c4cn(C)c5ccccc45)c(=O)c3=O)c2c1]

The compound was synthesized as described in method D from 3-chloro-4-(5-methoxy-1H-indol-3-yl)cyclobut-3-ene-1,2-dione (0.245 g, 0.90 mmol) and 1-methyl-1H-indole (0.190 mL, 1.52 mmol); yellow powder (Yield: 18%). $^1$H-NMR (600 MHz, DMSO-d$_6$): δ (ppm)=3.55 (s, 3H, CH$_3$), 3.98 (s, 3H, CH$_3$), 6.90 (dd, J=8.8, 2.5 Hz, 1H, ArH), 7.20 (ddd, J=8.0, 7.0, 1.0 Hz, 1H, ArH), 7.34 (ddd, J=8.2, 7.1, 1.1 Hz, 1H, ArH), 7.41-7.44 (m, 1H, ArH), 7.47 (dd, J=8.8, 0.5 Hz, 1H, ArH), 7.65 (dt, J=8.3, 0.9 Hz, 1H, ArH), 7.92 (dt, J=8.0, 1.0 Hz, 1H), 8.25 (s, 1H, ArH), 8.32 (s, 1H, ArH), 12.35 (s, 1H, NH).

Example 22: 3-(5-Bromo-1H-indol-3-yl)-4-(2-phenyl-1H-indol-3-yl)cyclobut-3-ene-1,2-dione (KuHL071)

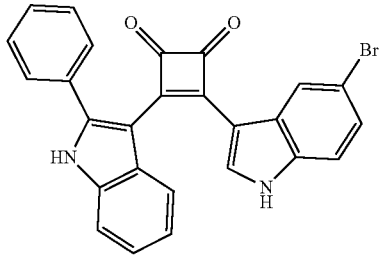 [SMILES: O=c1c(-c2c[nH]c3ccc(Br)cc23)c(-c2c(-c3ccccc3)[nH]c3ccccc23)c1=O]

The compound was synthesized as described in method D from 3-chloro-4-(2-phenyl-1H-indol-3-yl)cyclobut-3-ene-1,2-dione (0.309 g, 1.00 mmol) and 5-bromo-1H-indole (0.297 g, 1.52 mmol). Crystallization from ethyl acetate yielded a yellow-orange powder (Yield: 28%). $^1$H-NMR (400 MHz, DMSO-d$_6$): δ (ppm)=7.07-7.39 (m, 7H, ArH), 7.42-7.51 (m, 1H, ArH), 7.51-7.62 (m, 3H, ArH), 7.76 (s, 1H, ArH), 7.93 (d, J=13.7 Hz, 1H, ArH), 12.34 (s, 1H, NH), 12.51 (s, 1H, NH).

Example 23: 3-(5-Bromo-1H-indol-3-yl)-4-(2-methyl-1H-indol-3-yl)cyclobut-3-ene-1,2-dione (KuHL027)

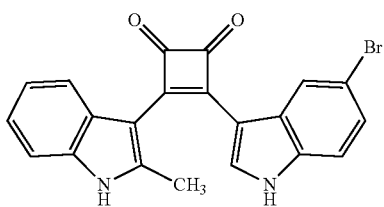 [SMILES: Cc1[nH]c2ccccc2c1-c1c(-c2c[nH]c3ccc(Br)cc23)c(=O)c1=O]

The compound was synthesized as described in method D from 3-chloro-4-(2-methyl-1H-indol-3-yl)cyclobut-3-ene-1,2-dione (0.245 g, 1.00 mmol) and 1-bromo-1H-indole (0.364 g, 1.86 mmol); yellow powder (Yield: 17%). $^1$H-NMR (600 MHz, DMSO-$d_6$): δ (ppm)=2.59 (s, 3H, CH$_3$), 7.00 (ddd, J=8.0, 7.1, 1.0 Hz, 1H, ArH), 7.09 (dt, J=7.9, 0.9 Hz, 1H, ArH), 7.18 (ddd, J=8.1, 7.1, 1.2 Hz, 1H, ArH), 7.37 (dd, J=8.6, 2.0 Hz, 1H, ArH), 7.44-7.54 (m, 2H, ArH), 7.83 (s, 1H, ArH), 8.14 (d, J=1.9 Hz, 1H, ArH), 12.24 (s, 1H, NH), 12.50 (s, 1H, NH).

Example 24: 3-(5-Bromo-1-methyl-1H-indol-3-yl)-4-(2-methyl-1H-indol-3-yl)cyclobut-3-ene-1,2-dione (KuHL077)

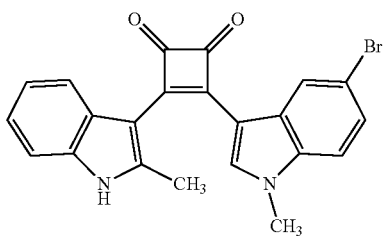 [SMILES: Cc1[nH]c2ccccc2c1-c1c(-c2cn(C)c3ccc(Br)cc23)c(=O)c1=O]

The compound was synthesized as described in method E from 3-chloro-4-(2-methyl-1H-indol-3-yl)cyclobut-3-ene-1,2-dione (0.246 g, 1.02 mmol) and 5-bromo-1-methyl-1H-indole (0.316 g, 1.50 mmol). Crystallization from ethanol/toluene yielded a yellow powder (Yield: 32%). $^1$H-NMR (400 MHz, DMSO-$d_6$): δ (ppm)=2.56 (s, 3H, CH$_3$), 3.88 (s, 3H, N—CH$_3$), 6.99 (ddd, J=8.0, 7.0, 1.1 Hz, 1H, ArH), 7.24-7.11 (m, 2H, ArH), 7.50-7.37 (m, 2H, ArH), 7.59 (d, J=8.7 Hz, 1H, ArH), 7.98 (s, 1H, ArH), 8.01 (d, J=1.9 Hz, 1H, ArH), 12.23 (s, 1H, NH).

Example 25: 3-(1-Methyl-1H-indol-3-yl)-4-(2-methyl-1H-indol-3-yl)cyclobut-3-ene-1,2-dione (KuHL050)

(X)

The compound was synthesized as described in method D from 3-chloro-4-(2-methyl-1H-indol-3-yl)cyclobut-3-ene-1,2-dione (0.221 g, 0.90 mmol) and 1-methyl-1H-indole (0.268 mL, 2.15 mmol); orange powder (Yield: 5%). $^1$H-NMR (600 MHz, DMSO-$d_6$): δ (ppm)=2.51 (s, 3H, CH$_3$), 3.91 (s, 3H, N—CH$_3$), 6.97 (ddd, J=8.1, 7.1, 1.0 Hz, 1H, ArH), 7.09 (ddd, J=8.0, 7.1, 1.0 Hz, 1H, ArH), 7.16 (ddd, J=8.1, 7.1, 1.1 Hz, 1H, ArH), 7.21 (dt, J=7.9, 0.9 Hz, 1H, ArH), 7.29 (ddd, J=8.2, 7.1, 1.1 Hz, 1H, ArH), 7.45 (dt, J=8.1, 0.9 Hz, 1H, ArH), 7.60 (dt, J=8.3, 0.9 Hz, 1H, ArH), 7.72 (d, J=8.0 Hz, 1H, ArH), 8.07 (s, 1H, ArH), 12.17 (s, 1H, NH).

Example 26: 3-(2-Methyl-1H-indol-3-yl)-4-(2-phenyl-1H-indol-3-yl)cyclobut-3-ene-1,2-dione (KuHL026)

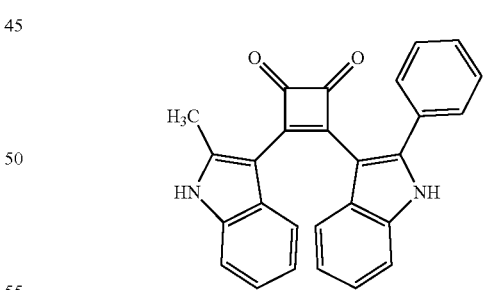

The compound was synthesized as described in method D from 3-chloro-4-(2-methyl-1H-indol-3-yl)cyclobut-3-ene-1,2-dione (0.244 g, 0.99 mmol) and 2-phenyl-1H-indole (0.403 g, 3.02 mmol). Crystallization from acetone yielded a yellow powder (Yield: 13%). $^1$H-NMR (400 MHz, DMSO-$d_6$): δ (ppm)=2.42 (s, 3H), 6.80 (ddd, J=8.0, 7.1, 1.0 Hz, 1H), 6.92 (d, J=8.0 Hz, 1H), 6.96-7.28 (m, 9H), 7.51 (dt, J=8.1, 0.9 Hz, 1H), 7.63-7.70 (m, 1H), 11.85 (s, 1H), 12.34 (s, 1H).

Example 27: 3-(1-Methyl-1H-indol-3-yl)-4-(2-phenyl-1H-indol-3-yl)cyclobut-3-ene-1,2-dione (KuHL072)

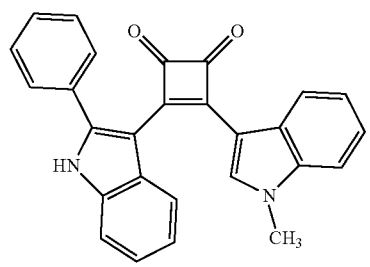

(XI)

The compound was synthesized as described in method E from 3-chloro-4-(2-phenyl-1H-indol-3-yl)cyclobut-3-ene-1,2-dione (0.310 g, 1.01 mmol) and 1-methyl-1H-indole (0.190 mL, 1.52 mmol). Crystallization from petroleum ether/acetone yielded a yellow-orange powder (Yield: 28%).

$^1$H-NMR (600 MHz, DMSO-$d_6$): δ (ppm)=3.70 (s, 3H, $CH_3$), 7.06-7.13 (m, 2H, ArH), 7.18-7.30 (m, 6H, ArH), 7.47 (dt, J=8.2, 0.9 Hz, 1H, ArH), 7.53-7.61 (m, 4H, ArH), 7.69 (s, 1H, ArH) 12.49 (s, 1H).

In table 1 the compounds of formula (I) according to the present invention synthesized herein are summarized wherein for A and M the position (pos) at the indole ring is identified. In addition, the table shows the example for the synthesis of the compounds.

| No. | A (pos) | M (pos) | E | L | R | Example |
|---|---|---|---|---|---|---|
| 1 | H | H | H | H | H | 1 (II) |
| 2 | Br (5) | Br (5) | H | H | H | |
| 3 | I (5) | I (5) | H | H | H | |
| 4 | Carbonitrile (5) | Carbonitrile (5) | H | H | H | |
| 5 | $H_3CO$ (5) | $OCH_3$ (5) | H | H | H | 2 |
| 6 | H | H | Phenyl | Phenyl | H | 3 (III) |
| 7 | H | H | $CH_3$ | $CH_3$ | H | 4 |
| 8 | H | Cl (5) | H | H | H | 5 |
| 9 | H | Br (5) | H | H | H | 6 (IV) |
| 10 | H | I (5) | H | H | H | 7 |
| 11 | H | Carbonitrile (5) | H | H | H | 8 |
| 12 | H | Benzyloxy (5) | H | H | H | |
| 13 | H | H | H | Phenyl | H | 9 (V) |
| 14 | H | $OCH_3$ (5) | H | H | H | 10 |
| 15 | H | H | H | $CH_3$ | H | 11 |
| 16 | H | H | H | H | $CH_3$ | 12 (VI) |
| 17 | $H_3CO$ (5) | F (5) | H | H | H | 13 |
| 18 | $H_3CO$ (5) | Cl (5) | H | H | H | 14 (VII) |
| 19 | $H_3CO$ (5) | Cl (7) | H | H | H | |
| 20 | $H_3CO$ (5) | Br (4) | H | H | H | |
| 21 | $H_3CO$ (5) | Br (5) | H | H | H | 15 (VIII) |
| 22 | $H_3CO$ (5) | Br (6) | H | H | H | |
| 23 | $H_3CO$ (5) | Br (7) | H | H | H | |
| 24 | $H_3CO$ (5) | Br (5) | H | H | $CH_3$ | |
| 25 | $H_3CO$ (5) | I (5) | H | H | H | 16 (IX) |
| 26 | $H_3CO$ (5) | Carbonitrile (5) | H | H | H | 17 |
| 27 | $H_3CO$ (5) | Benzyloxy (5) | H | H | H | 18 |
| 28 | $H_3CO$ (5) | H | Phenyl | H | H | 19 |
| 29 | $H_3CO$ (5) | H | H | $CH_3$ | H | 20 |
| 30 | $H_3CO$ (5) | H | H | H | $CH_3$ | 21 |
| 31 | H | Br (5) | Phenyl | H | H | 22 |
| 32 | Br (5) | H | H | H | $CH_3$ | |
| 33 | H | Br (5) | $CH_3$ | H | H | 23 |
| 34 | H | Br (5) | $CH_3$ | H | $CH_3$ | 24 |
| 35 | H | H | $CH_3$ | H | $CH_3$ | 25 (X) |
| 36 | H | H | $CH_3$ | Phenyl | H | 26 |
| 37 | H | H | Phenyl | H | $CH_3$ | 27 (XI) |

Bioactivity Assay

Erythrocytic stages of transgenic NF54-luc *P. falciparum* were used for the luciferase-based viability assay. First, the culture was dispensed in triplicate into white 96-well flat bottom plates (each well contains 250 ul) (NUNC, Denmark) with parasitemia of 0.5-1%. Then the cultures were incubated in the presence of a 30 μM concentration of the test compounds for 48 hours (37° C., 90% $N_2$, 5% $CO_2$, and 5% $O_2$). Subsequently, 100 ul RPMI1640 media was removed from each well and a 100 μL volume of the Bright-Glo® substrate solution was added to each well. One of the cleavage products of the reaction is light, which was measured by a FLUOROSKAN FL luminometer (Thermo) machine; thereby detecting the amount of living parasites. In case the inhibition of the proliferation exceeded 50%, the experiments were repeated with 3 μM solutions. If the growth then was also inhibited by at least 25%, titrations were carried out to determine the $EC_{50}$ value of the compounds. The $EC_{50}$ value is the half maximal effective concentration (the concentration at which half maximal inhibition is observed). Untreated cultures were used as negative controls and to calculate the inhibition rate (0% inhibition of parasite growth). Blasticidin (Sigma-Aldrich, St. Louis, Mo.), a drug used for selection of transfected parasites, was included as a positive control on each plate and gave >90% inhibition of parasite growth at 2 μg/mL.

The results of the assays are depicted in Table 1.

TABLE 1

$EC_{50}$ values [μM] and activity [% inhibition] at 3 μM and 30 μM on *P. falciparum*.

| No. | Compound | $EC_{50}$ [μM], *P. falciparum* | Inhibition, *P. falciparum* [%] at 3 μM | Inhibition, *P. falciparum* [%] at 30 μM |
|---|---|---|---|---|
| 1 | KuHL043 (II) | 8.33 | 17.9 ± 3.3 | 99.2 ± 0.2 |
| 5 | KuHL048 | | 19.7 ± 3.6 | 79.3 ± 1.3 |
| 6 | KuHL009 (III) | 2.47 | 41.1 ± 0.6 | 98.9 ± 0.8 |
| 7 | KuHL012 | | 18.3 ± 6.3 | 77.8 ± 5.9 |
| 8 | KuHL118 | | 44.7 ± 0.5 | |
| 9 | KuHL037 (IV) | 3.02 | 65.9 ± 1.8 | 99.5 ± 0.4 |
| 10 | KuHL117 | | 31.3 ± 2.7 | |
| 11 | KuHL122 | | 26.8 ± 1.6 | |
| 13 | KuHL044 (V) | 6.38 | 65.0 ± 2.8 | 99.7 ± 0.1 |
| 14 | KuHL049 | | 18.3 ± 5.0 | |
| 15 | KuHL025 | >30 | 23.4 ± 5.4 | 98.8 ± 0.5 |
| 16 | KuHL032 (VI) | 2.97 | 52.0 ± 1.8 | 98.7 ± 1.1 |
| 17 | KuHL113 | | 19.3 ± 3.1 | |
| 18 | KuHL102 (VII) | 1.52 | 87.0 ± 0.5 | |
| 21 | KuHL047 (VIII) | 0.47 | 100 ± 0 | 98.8 ± 0.7 |
| 25 | KuHL101 (IX) | 0.65 | 99.1 ± 0.4 | |
| 26 | KuHL103 | | 26.8 ± 1.1 | |
| 27 | KuHL136 | | 21.7 ± 2.5 | |
| 28 | KuHL058 | | 22.4 ± 2.7 | |
| 29 | KuHL018 | 10.0 | 34.2 ± 8.0 | 99.6 ± 0.2 |
| 30 | KuHL057 | | | 13.6 ± 3.9 |
| 31 | KuHL071 | | 16.0 ± 0.7 | |
| 33 | KuHL027 | 30.5 | 45.6 ± 1.8 | 99.3 ± 0.4 |
| 34 | KuHL077 | | 12.7 ± 2.8 | |
| 35 | KuHL050 (X) | 2.67 | 59.6 ± 0.2 | 99.3 ± 0.3 |

TABLE 1-continued

EC$_{50}$ values [μM] and activity [% inhibition] at 3 μM and 30 μM on *P. falciparum*.

| No. | Compound | EC$_{50}$ [μM], *P. falciparum* | Inhibition, *P. falciparum* [%] at 3 μM | Inhibition, *P. falciparum* [%] at 30 μM |
|---|---|---|---|---|
| 36 | KuHL026 | 9.26 | 41.1 ± 1.7 | 98.4 ± 0.5 |
| 37 | KuHL072 (XI) | 1.72 | 67.7 ± 0.7 | |

The invention claimed is:

1. A compound of formula (I)

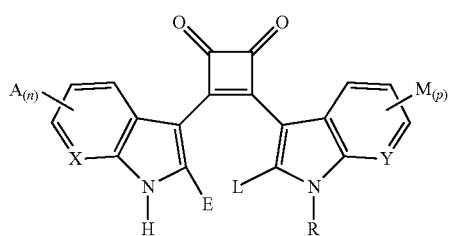

(I)

wherein X, Y are independently of each other, C, N or C—R;
L is hydrogen, C$_1$-C$_8$ alkyl, C$_1$-C$_8$ alkyloxy, aryloxy, halogen, formyl, aryl, heteroaryl, heterocycloalkyl, acyl, hydroxy C$_1$-C$_8$ alkyl, halo C$_1$-C$_8$ alkyl, amino C$_1$-C$_8$ alkyl;
E is hydrogen, C$_1$-C$_8$ alkyl, C$_1$-C$_8$ alkyloxy, aryloxy, halogen, formyl, aryl, heteroaryl, heterocycloalkyl, acyl, hydroxy C$_1$-C$_8$ alkyl, halo C$_1$-C$_8$ alkyl, amino C$_1$-C$_8$ alkyl;
A is independently of each other, halogen, hydroxyl, amino, monoalkylamino, dialkylamino, sulfanyl, sulfinyl, sulfonyl, aminosulfonyl, carboxyl, C$_1$-C$_8$ alkyloxyl, aryloxy, nitro, cyano, C$_1$-C$_8$ alkyl, amino C$_1$-C$_8$ alkyl, hydroxy C$_1$-C$_8$ alkyl, halo C$_1$-C$_8$ alkyl, C$_1$-C$_8$ alkyloxy, carbonylamino, aminocarbonyl, acyl, formyl, aryl, heteroaryl, heterocycloalkyl;
M is independently of each other, halogen, hydroxyl, amino, monoalkylamino, dialkylamino, sulfanyl, sulfinyl, sulfonyl, aminosufonyl, carboxyl, C$_1$-C$_8$ alkyloxyl, aryloxy, nitro, cyano, C$_1$-C$_8$ alkyl, amino C$_1$-C$_8$ alkyl, hydroxy C$_1$-C$_8$ alkyl, halo C$_1$-C$_8$ alkyl, halo C$_1$-C$_8$ alkyloxy, carbonylamino, aminocarbonyl, acyl, formyl, aryl, heteroaryl, heterocycloalkyl;
R is hydrogen, Z or Q;
Z is C$_1$-C$_8$ alkyl, hydroxy C$_1$-C$_8$ alkyl, methoxy C$_1$-C$_8$ alkyl, halo C$_1$-C$_8$ alkyl, amino C$_1$-C$_8$ alkyl, acyl, sulfinyl C$_1$-C$_8$ alkyl, sulfonyl C$_1$-C$_8$ alkyl;
Q is aryl or heteroaryl or heterocycloalkyl, which may be substituted by a substituent as listed for Z;
n is 0 or is an integer of 1, 2, or 3,
p is 0 or is an integer of 1, 2, or 3,
or a salt or solvate thereof.

2. A compound of formula (I) according to claim 1, wherein R is C$_1$-C$_3$ alkyl or hydrogen.

3. The compound of formula (I) according to claim 1, wherein M is independently selected from halogen, cyano, C$_1$-C$_3$ alkyl, phenyl, or C$_1$-C$_3$ alkoxy and/or A is independently selected from halogen, cyano, C$_1$-C$_3$ alkyl, phenyl, or C$_1$-C$_3$ alkoxy.

4. The compound of formula (I) according to claim 1, wherein L and/or E are independently of each other hydrogen, C$_1$-C$_3$ alkyl, or phenyl.

5. The compound of formula (I) according to claim 1, wherein X and Y are C.

6. The compound of formula (I) according to claim 1, wherein n and/or p are independently of each other 1 or 0.

7. The compound of formula (I) according to claim 1, wherein X is C, Y is C, R is H or CH$_3$, A is CH$_3$, phenyl or Cl, Br or I, M is CH$_3$, phenyl or Cl, Br or I, E is CH$_3$, hydrogen or phenyl, L is CH$_3$, hydrogen or phenyl, and n is 0 or 1.

8. The compound of formula (I) according to claim 1, wherein said compound is selected from the compounds of formula (II) to (XI)

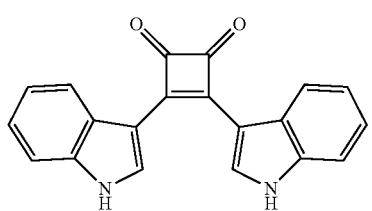

(II)

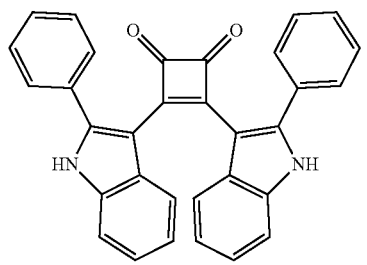

(III)

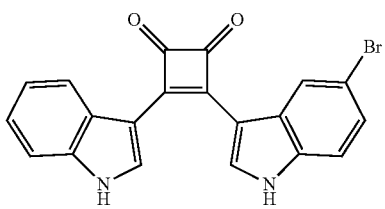

(IV)

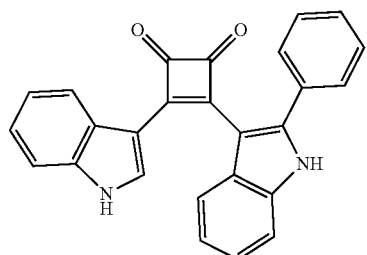

(V)

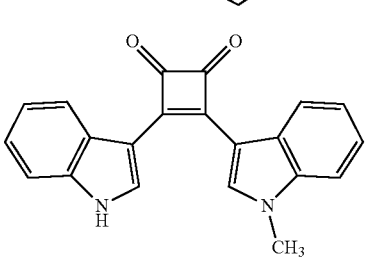

(VI)

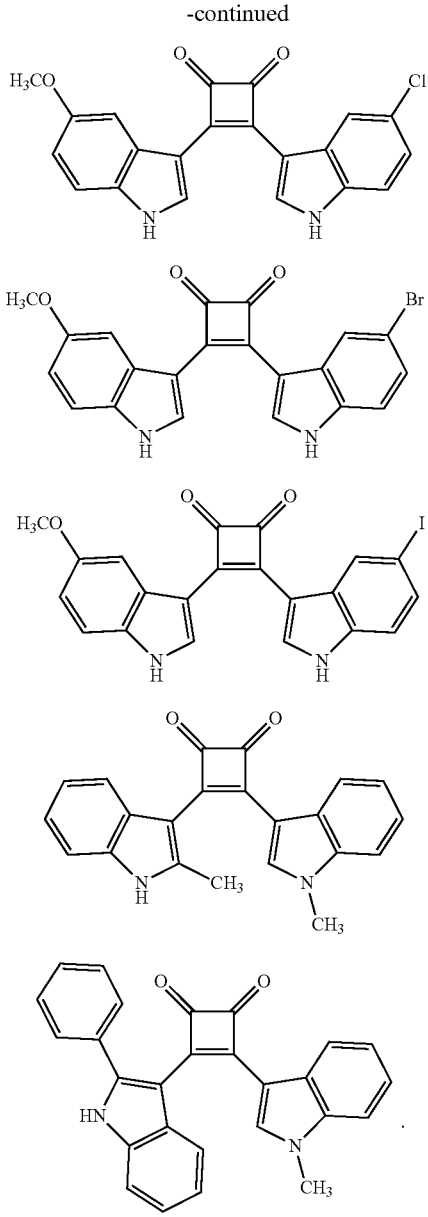

9. A pharmaceutical composition comprising one or more compounds of formula (I) as defined in claim 1.

10. The pharmaceutical composition of claim 9, wherein said one or more compounds are the only pharmaceutical active agents comprised in said pharmaceutical composition.

11. The pharmaceutical composition according to claim 9, containing at least one further antiprotozoal active agent.

12. The pharmaceutical composition according to claim 11, wherein the at least one further antiprotozoal active agent is selected from the group of fluoroquinolone derivatives, artemisinin derivatives, artemether, artemotil, artesunate, artelinic acid, dihydroartemisinine, chloroquine, proguanil, mefloquine, lumefantrine, quinine, doxycycline, halofantrine, primaquine, sulfadoxine, tetracycline, pyrimethamine, atovaquone, cycloguanil.

13. The pharmaceutical composition according to claim 9, whereby the one or more compounds of formula (I) is adapted for oral, parenteral, dermal or inhalatory administration.

14. The pharmaceutical composition according to claim 9, adapted for simultaneous, separate or sequential administration.

15. The pharmaceutical composition according to claim 11, wherein the compound of formula (I) is present in a sub antiprotozoal dosage and the at least one further antiprotozoal active agent is present in a sub antiprotozoal dosage.

16. A method for treating malaria caused by *Plasmodium* comprising the step of administering a compound of formula (I) as defined in claim 1 to a subject in need thereof.

17. The method for treating malaria caused by *Plasmodium* according to claim 16, wherein said compound of formula (I) is a compound of formulae (II) to (XI) as defined in claim 8.

18. The method for treating malaria caused by *Plasmodium* according to claim 16, wherein said *Plasmodium* is *Plasmodium falciparum*.

19. A method for treating malaria caused by *Plasmodium* comprising the step of administering a pharmaceutical composition according to claim 9 to a subject in need thereof.

20. The compound of formula (I) according to claim 1, wherein L is phenyl.

21. The compound of formula (I) according to claim 1, wherein L is pyridyl.

22. The compound of formula (I) according to claim 1, wherein E is phenyl.

23. The compound of formula (I) according to claim 1, wherein E is pyridyl.

24. The compound of formula (I) according to claim 1, wherein A is trifluoromethyl.

25. The compound of formula (I) according to claim 1, wherein A is trifluoromethoxy.

26. The compound of formula (I) according to claim 1, wherein A is phenyl.

27. The compound of formula (I) according to claim 1, wherein A is pyridyl.

28. The compound of formula (I) according to claim 1, wherein M is trifluoromethyl.

29. The compound of formula (I) according to claim 1, wherein M is trifluoromethoxy.

30. The compound of formula (I) according to claim 1, wherein M is phenyl.

31. The compound of formula (I) according to claim 1, wherein M is pyridyl.

32. The compound of formula (I) according to claim 1, wherein Q is phenyl.

33. The compound of formula (I) according to claim 4, wherein L and/or E are independently of each other $CH_3$.

* * * * *